US010583290B2

(12) United States Patent
McCarthy et al.

(10) Patent No.: US 10,583,290 B2
(45) Date of Patent: Mar. 10, 2020

(54) ENHANCING VISION FOR A VISION IMPAIRED USER

(71) Applicant: National ICT Australia Limited, Eveleigh, New South Wales (AU)

(72) Inventors: Chris McCarthy, Eveleigh (AU); Nick Barnes, Eveleigh (AU)

(73) Assignee: National ICT Australia Limited, Eveleigh, New South (AU)

( * ) Notice: Subject to any disclaimer, the term of this patent is extended or adjusted under 35 U.S.C. 154(b) by 222 days.

(21) Appl. No.: 15/510,187

(22) PCT Filed: Sep. 10, 2015

(86) PCT No.: PCT/AU2015/050537
§ 371 (c)(1),
(2) Date: Mar. 9, 2017

(87) PCT Pub. No.: WO2016/037238
PCT Pub. Date: Mar. 17, 2016

(65) Prior Publication Data
US 2017/0259060 A1    Sep. 14, 2017

(30) Foreign Application Priority Data
Sep. 10, 2014    (AU) .............................. 2014903623

(51) Int. Cl.
*A61N 1/36*        (2006.01)
*H04N 5/243*       (2006.01)
*A61N 1/05*        (2006.01)

(52) U.S. Cl.
CPC ....... *A61N 1/36046* (2013.01); *A61N 1/0531* (2013.01); *A61N 1/0543* (2013.01); *A61N 1/0548* (2013.01); *H04N 5/243* (2013.01)

(58) Field of Classification Search
CPC .............. A61N 1/36046; A61N 1/0548; A61N 1/0543; A61N 1/0531
See application file for complete search history.

(56) References Cited

U.S. PATENT DOCUMENTS 8,330,768 B2    12/2012  Mantiuk et al.
2014/0085447 A1*  3/2014  Lorach ................. A61N 1/0543
                                              348/62
2017/0079770 A1*  3/2017  Li ....................... A61N 1/36046

FOREIGN PATENT DOCUMENTS

EP         1918871 A1    4/2014
WO    WO 2009/126258 A1  10/2009
WO    WO 2012/085163 A1   6/2012

OTHER PUBLICATIONS

Li et al, "On Just Noticeable Difference for Bionic Eye", 34th Annual International Conference of the IEEE EMBS, Sep. 2012.*
(Continued)

*Primary Examiner* — George R Evanisko
(74) *Attorney, Agent, or Firm* — Kilpatrick Townsend & Stockton LLP

(57) ABSTRACT

The present disclosure provides a computer-implemented method for enhancing vision for a vision impaired user. The method comprises, for a point in an input image, determining (210) a weight for the point based on visual importance of the point in the input image; comparing (220) the weight for the point to a threshold; and if the weight for the point meets the threshold, determining (230) a first output value for an imaging element of a vision enhancement apparatus so that a difference between the first output value and an intensity level of a portion of the input image neighbouring the point increases with the weight, wherein the difference is at least one Just-Noticeable-Difference of the vision enhancement apparatus, such that when the first output value is applied to the imaging element of the vision enhancement (Continued)

apparatus to create a first visual stimulus, the first visual stimulus is substantially perceivable by the vision impaired user.

27 Claims, 18 Drawing Sheets

(56) References Cited

OTHER PUBLICATIONS

International Search Report (4 pages) and Written Opinion (4 pages) dated Nov. 17, 2015, prepared by the Australian Patent Office as International Searching Authority for PCT International Patent Application No. PCT/AU2015/050537.

McCarthy, C., et al., "Importance Weighted Image Enhancement for Prosthetic Vision," IEEE International Symposium on Mixed and Augmented Reality 2014 Science and Technology Proceedings, Sep. 10-12, 2014, Munich, Germany, pp. 45-51.

Horne, L., et al., "Image Segmentation for Enhancing Symbol Recognition in Prosthetic Vision," 34th Annual International Conference of the IEEE EMBS, San Diego, California USA, Aug. 28-Sep. 1, 2012, pp. 2792-2795.

Liu, W., et al., "Image Processing and Interface for Retinal Visual Prostheses," IEEE International Symposium on Circuits and Systems, 2005. ISCAS 2005, May 23-26, 2005, pp. 2927-2930, vol. 3.

Feng, D., et al., "Enhancing scene structure in prosthetic vision using iso-disparity contour perturbance maps," 35th Annual International Conference of the IEEE EMBS, Osaka, Japan, Jul. 3-7, 2013, pp. 5283-5286.

Hicks et al., A Depth-Based Head-Mounted Visual Display to aid Navigation in Partially Sighted Individuals, PLOS ONE, Jul. 2013, vol. 8, Issue 7.

Ferradans et al., An Analysis of Visual Adaptation and Contrast Perception for Tone Mapping, IEEE Transactions on Pattern Analysis and Machine Intelligence, pp. 2002-2012, Oct. 2011.

McCarthy et al., Adaptive Image Contrast Enhancement Based on Human Visual Properties, IEEE Transactions on Medical Imaging, vol. 13, No. 4, Dec. 1994, pp. 573-586.

Extended European Search Report of PCT/AU2015/050537) dated Jun. 6, 2018, all pages.

Yi Li et al: "On Just Noticeable Difference for Bionic Eye", Engineering in Medicine and Biology Society (EMBC), 2013 35th Annual International Conference of the IEEE, IEEE, Aug. 28, 2012 (Aug. 28, 2012), pp. 2961-2964, XP032463561, ISSN: 1557-170X, DOI: 10.1109/EMBC.2012.6346585.

McCarthy et al., Ground Surface Segmentation for Navigation with a Low Resolution Visual Prosthesis, NICTA Canberra Research Laboratory, Canberra ACT, Australia and College of Engineering and Computer Science, Australian National University, Canberra ACT, Australia. (2011).

Liu et al., Transformative Reality: Augmented Reality for Visual Prostheses, IEEE International, Science and Technology Proceedings, Oct. 26-29, Basel, Switzerland. (2011).

McCarthy et al., Augmenting Intensity to Enhanced Scene Structure in Prosthetic Vision, Computer Vision Research Group, NICTA, Canberra ACT, Australia and College of Engineering and Computer Science, Australian National University, Canberra ACT, Australia. (2013).

\* cited by examiner

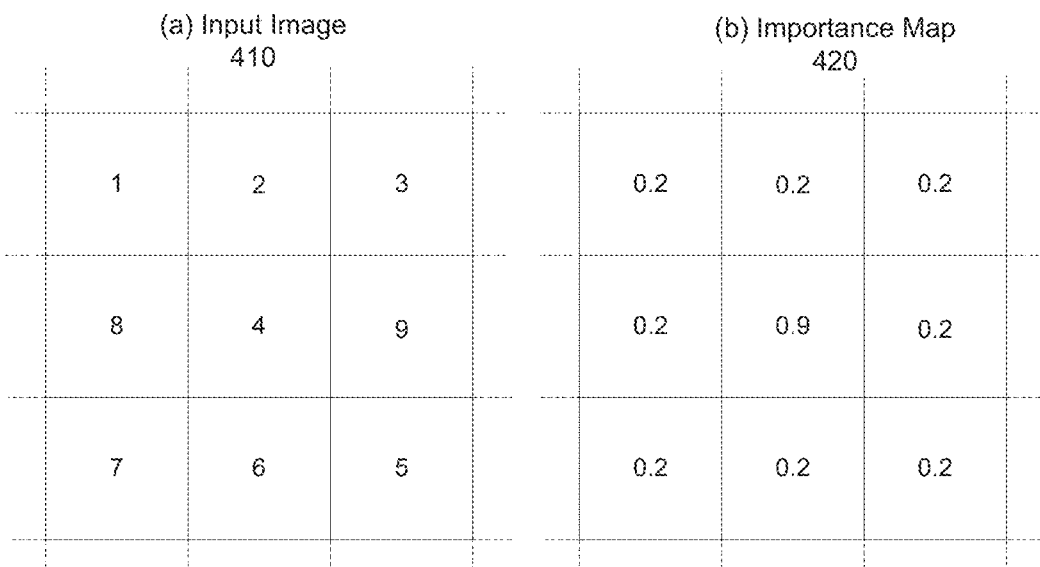
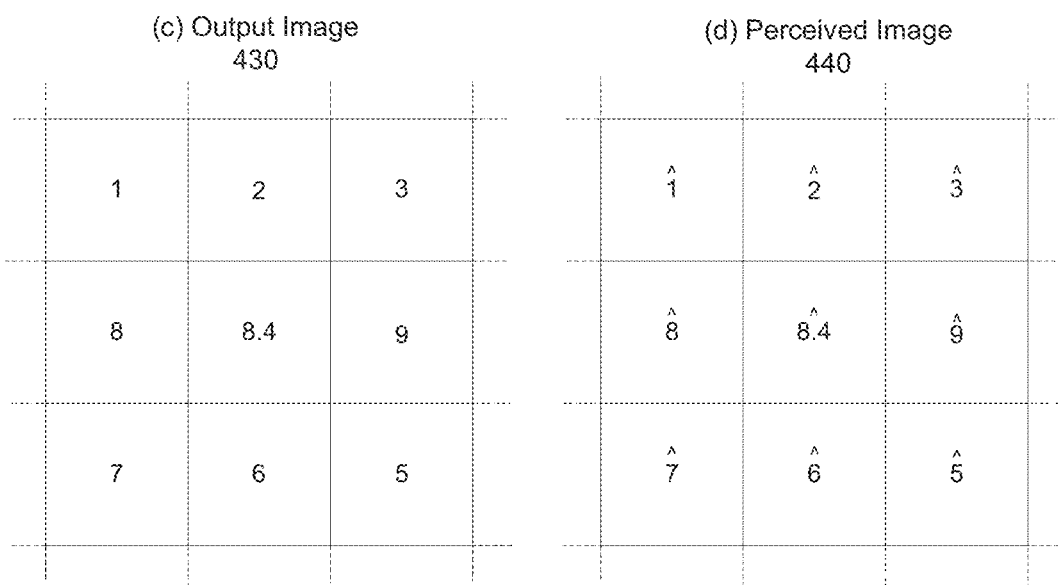
Fig. 4

Fig. 12 Looming object enhancement showing (a) samples from the original sequence, (b) the resulting enhancement at full resolution (8 brightness levels), and simulated prosthetic vision renderings of the (c) histogram equalised original image, and (d), the The method according to present disclosure (st = 0:2).

ENHANCING VISION FOR A VISION IMPAIRED USER

CROSS-REFERENCE TO RELATED APPLICATIONS

The present application is a national phase of PCT International Application Number PCT/AU2015/050537, filed on Sept. 10, 2015, which claims the benefit of Australian Provisional Patent Application Number 2014903623, filed on Sept. 10, 2014. Each of these applications is hereby incorporated by reference in its entirety for all purposes.

TECHNICAL FIELD

The present disclosure generally relates to vision enhancement methods and devices. The present disclosure includes computer-implemented methods, software, computer systems for enhancing vision for a vision impaired user.

BACKGROUND

A person's vision may be impaired due to degeneration of photoreceptor cells in the retina of the person. As a result, the person becomes less sensitive to optical signals from surrounding environments. This kind of vision impairment may be treated by a vision aid system.

The vision aid system typically includes a camera and a vision enhancement apparatus. The vision enhancement apparatus comprises a plurality of imaging elements, for example, electrodes.

The camera receives the optical signals from the surrounding environments and represents the optical signals with visual signals, for example visual intensity levels of points of an image. The vision enhancement apparatus receives visual signals from the camera and translates the visual signals into electric current or voltage signals and applies these electric signals to the imaging elements. Each of the imaging elements may correspond to one or more points in the image. This way, vision-related tissues of the person (for example, a retina of the person) may be stimulated by the electric signals and a visual perception of the optical signals is generated for the person. The imaging elements may also be an array of motors that are placed on the back of the person. When supplied with the electrical signals, the array of motors generates vibrations corresponding to the optical signals so as to cause the person to perceive the optical signals in the form of tactility.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present disclosure is not to be taken as an admission that any or all of these matters form part of the prior art base or were common general knowledge in the field relevant to the present disclosure as it existed before the priority date of each claim of this application.

SUMMARY

There is provided a computer-implemented method for enhancing vision for a vision impaired user, the method comprising:

for a point in an input image, determining a weight for the point based on visual importance of the point in the input image;

comparing the weight for the point to a threshold; and if the weight for the point meets the threshold, determining a first output value for an imaging element of a vision enhancement apparatus so that a difference between the first output value and an intensity level of a portion of the input image neighbouring the point increases with the weight, wherein the difference is at least one Just-Noticeable-Difference of the vision enhancement apparatus, such that when the first output value is applied to the imaging element of the vision enhancement apparatus to create a first visual stimulus, the first visual stimulus is substantially perceivable by the vision impaired user.

It is an advantage of the method that the contrast between the important point and the neighbouring points increases with the importance of the point, such that the more important the point is, the more perceivable the point is to the vision impaired user, which provide useful visual guidance for the vision impaired user. It is clear that this leads to an improvement to the technical field of visual enhancement (rather than the computer itself).

The method can also lead to improvements of a particular machine since the imaging elements of the vision enhancement apparatus are a machine with specific purposes achieved by hardware specific design. For example, the imaging elements of the vision enhancement apparatus include an array of electrodes that are implanted in vision-related tissues of the vision-impaired user. The array of electrodes may be implanted at different locations of intraocular tissues of the vision impaired user, for example, the subretinal location (behind the retina), the epiretinal location (on the retina), the intra-scleral location, or in the suprachoroidal space. The array of electrodes may also be implanted at any other suitable locations, for example, the cerebral cortex of the brain of the vision impaired user. The array of electrodes can also be placed on the tongue of the vision impaired user. The imaging elements of the vision enhancement apparatus may also include an array of motors that are placed on the suitable part of the body on the vision impaired user, for example, the back or chest of the vision impaired user.

The intensity level of the portion of the input image neighbouring the point may be an average intensity level of points in the portion of the input image.

If an intensity level of the point is greater than the intensity level of the portion of the input image, the first output value may be greater than the intensity level of the portion of the input image.

If the intensity level of the point is less than the intensity level of the portion of the input image, the first output value may be less than the intensity level of the portion of the input image.

If the intensity level of the point is equal to the intensity level of the portion of the input image, the first output value may be such that the difference is at least one Just-Noticeable-Difference of the vision enhancement apparatus.

The computer-implemented method may further comprise:

determining a difference between the intensity level of the point and the intensity level of the portion of the input image, if the difference is greater than at least one Just-Noticeable-Difference of the vision enhancement apparatus, the first output value for the imaging element is equal to the intensity level of the point.

The computer-implemented method may further comprise:
  determining the Just-Noticeable-Difference of the vision enhancement apparatus based on a Weber fraction and the intensity level of the portion of the input image.

The difference between the first output value and the intensity level of the portion of the input image neighbouring the point exponentially may increase with the weight.

The computer-implemented method may further comprise:
  if the weight does not meet the threshold, determining a second output value for the imaging element based on the weight and the threshold, such that a difference between the second output value and the intensity level of the portion of the input image is less than a difference between the intensity level of the point and the intensity level of the portion of the input image, such that when the second output value is applied to the imaging element to create a second visual stimulus, the second visual stimulus is less perceivable by the vision impaired user.

If the intensity level of the point is greater than the intensity level of the portion of the input image, the second output value may be greater than the intensity level of the portion of the input image.

If the intensity level of the point is less than the intensity level of the portion of the input image, the second output value may be less than the intensity level of the portion of the input image.

If the intensity level of the point is equal to the intensity level of the portion of the input image, the second output value may be determined to the intensity level of the point.

The computer-implemented method may further comprise:
  if the weight does not meet the threshold, determining a third output value for the imaging element that is equal to the intensity level of the point.

The computer-implemented method may further comprise:
  down-sampling the input image to match a resolution of the vision enhancement apparatus.

There is provided a computer software program, including machine-readable instructions, when executed by a processor, causes the processor to perform one or more methods described above where appropriate.

There is provided a computer system for enhancing vision for a vision impaired user, the computer system comprising:
  a memory to store instructions;
  a processor to perform the instructions from the memory
    for a point in an input image, to determine a weight for the point based on visual importance of the point in the input image;
    to compare the weight for the point to a threshold; and
    if the weight for the point meets the threshold, to determine a first output value for an imaging element of a vision enhancement apparatus so that a difference between the first output value and an intensity level of a portion of the input image neighbouring the point increases with the weight,
  wherein the difference is at least one Just-Noticeable-Difference of the vision enhancement apparatus, such that when the first output value is applied to the imaging element of the vision enhancement apparatus to create a first visual stimulus, the first visual stimulus is substantially perceivable by the vision impaired user.

BRIEF DESCRIPTION OF THE DRAWINGS

Features of the present disclosure are illustrated by way of non-limiting examples, and like numerals indicate like elements, in which:

FIG. 4($a$) is an example input image;

FIG. 4($b$) is an example importance map;

FIG. 4($c$) is an example output image according to the present disclosure;

FIG. 4($d$) is an example perceived image when the output image shown in FIG. 4($c$) is applied to a vision enhancement apparatus;

BEST MODES OF THE INVENTION

In an example described in the present disclosure, the imaging elements of the vision enhancement apparatus include an array of electrodes implanted at a suitable location in the body of the vision impaired user. For example, the array of electrode may be implanted in vision-related tissues of the vision-impaired user. Particularly, the array of electrodes can be implanted at different locations of intraocular tissues of the vision-impaired user, for example, near the retina of the vision-impaired user. The array of electrodes is supplied with electrical signals that are translated from the visual signals by the vision enhancement apparatus to stimulate the retina of the vision-impaired user to cause the user to perceive the optical signals. The array of electrodes may also be implanted in direct connection with the cerebral cortex of the brain of the vision-impaired user to stimulate the visual cortex. The array of electrodes can also be placed on the tongue of the vision impaired user to stimulate the tongue in order to cause the optical signals to be perceived by the vision-impaired user in the form of tactility.

In another example described in the present disclosure, the imaging elements of the vision enhancement apparatus include an array of motors that are placed on a suitable location on the body of the vision impaired user. For example, the array of motors may be place on the back or chest of the vision-impaired user. The electrical signals that are translated from the visual signals by the vision enhancement apparatus are used to drive the array of motors. As a result, vibrations generated by the array of motor cause the optical signals to be perceived by the vision-impaired user in the form of tactility.

Figure 1:
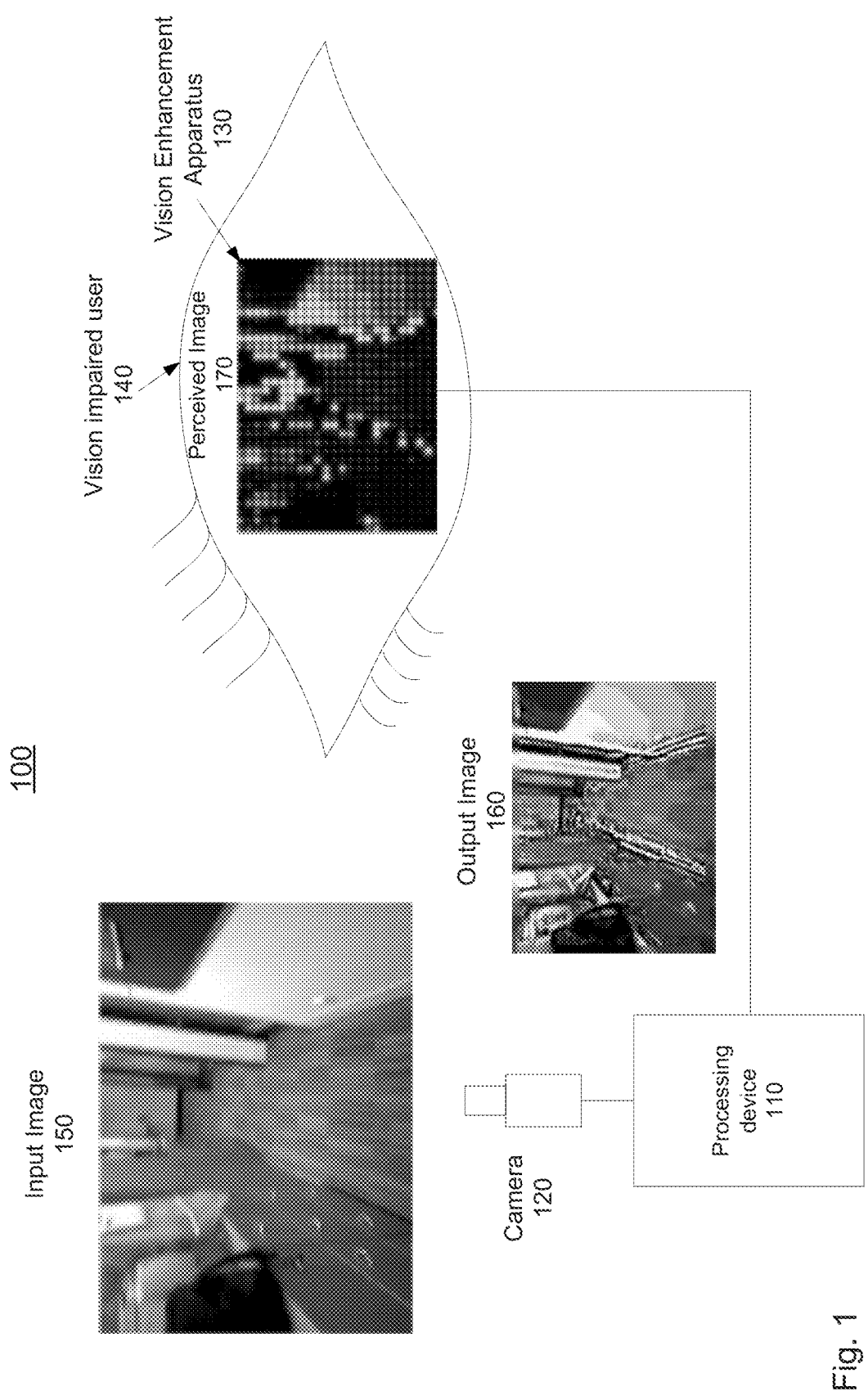
FIG. 1 is an example vision aid system according to the present disclosure.

FIG. 1 is an example vision aid system 100 according to the present disclosure.

The vision aid system 100 comprises a processing device 110, a camera 120 and a vision enhancement apparatus 130. The camera 120 is connected to the process device 120, which is in turn connected to the vision enhancement apparatus 130. The vision aid system 100 is illustrated in more detail in FIG. 13. In this example, the vision enhancement apparatus 130 is implanted at the subretinal location. That is, the vision enhancement apparatus 130 is implanted behind the retina. It should be noted that the vision enhancement apparatus 130 can be implanted at the epiretinal location (on the retina) or the intra-scleral location, or in the suprachoroidal space, or any other suitable locations, for example, the cerebral cortex of the brain of the vision-impaired user, without departing from the scope of the present disclosure.

These entities as shown in FIG. 1 may be connected by electric wires or wirelessly. Although these entities are shown as separate entities, one element may be part of another. For example, the processing device 110 may be part of the camera 120. It should be noted that the vision aid system 100 may also include other sensors that may contribute to formation of an importance map, for example, a depth sensor, inertial/gravity sensors, etc. The importance map will be discussed in detail hereinafter.

The vision aid system 100 may be worn by a user who needs to enhance their vision perception capabilities, for example, a vision impaired user 140, to see or perceive features that the user would see or perceive if their vision were normal.

The features may physically exist in a physical environment or scene that the vision impaired user 140 is in, for example, floor, chairs in a typical indoor environment, or street poles, vehicles in a typical outdoor environment. The features may also conceptually exist in a media being viewed by the vision impaired user 140. For example, a photo or a video being viewed may contain features that may or may not exist in a physical environment.

In spite of the form of existence of the features, it is relatively easy for a person with healthy eyes to perceive these features, nevertheless it may be difficult for the vision impaired user 140 to perceive these features since the degenerated photoreceptor cells in the retina of the vision impaired user 140 do not provide sufficient contrast between the features and neighbouring areas of the features.

Specifically, in the example shown in FIG. 1, an input image 150 is captured by the camera 110 of the vision aid system 100. The input image 150 may represent what the vision impaired user 140 would see if the vision of the user 140 were not impaired, whether it be a physical environment that the user 40 is in or a media that is being viewed by the user 140. For easy description, the input image 150 is deemed in the present disclosure to represent a physical environment that the vision impaired user 140 is in.

It can be seen from FIG. 1 that the input image 150 contains features that may be important to safety. These features may include objects for example, doors, floor, walls, shelves. These features may also include boundaries between these objects. It is relatively easy for a healthy person to perceive these features when moving in the scene represented by the input image 150. Therefore, the healthy person can move on the floor without running into the shelves, walls or other obstacles.

However, as the contrast between the features and neighbouring areas of the features in the input image 150 might not be sufficient for the vision impaired user 140 to accurately perceive existence of these features, which may be due to the visual intensity levels of the features are similar to those of the neighbouring areas of the features, if the input image 150 is directly applied to the vision enhancement apparatus 130, the scene that is actually perceived by the vision impaired user 140 may appear to be blurred.

For example, the intensity levels of the shelves and the walls in the input image 150 are similar to those of the floor, which makes it difficult for the vision impaired user 140 to be aware that there are separate objects in the scene for lack of visual boundaries between the shelves or the walls and the floor. As a result, the vision impaired user 140 may run into the shelves or the walls when moving in scene.

Therefore, in the present disclosure, before the input image 150 is applied to the vision enhancement apparatus 130, the input image 150 is sent to the processing device 110 to enhance the contrast of the input image 150 in order to make existence of important features perceivable to the vision impaired user 140.

Specifically, the processing device 110 determines a weight for each point of the image to indicate importance of the point and adjusts the visual intensity level of the point based on the weight.

If the weight meets a threshold, the processing device 110 adjusts an intensity level of the point such that a difference between the adjusted intensity level of the point and an intensity level of neighbouring points of the point is at least one Just-Noticeable-Difference of the vision enhancement apparatus 130 and the difference increases with the importance weight of the point. This way, the contrast between the important point and the neighbouring points are enhanced.

On the other hand, if the weight does not meet the threshold, the processing device 110 adjusts the intensity level of the point such that the difference between the intensity level of the point and the intensity level of neighbouring points of the point is reduced. This way, the contrast between the unimportant point and the neighbouring points are attenuated.

The adjusted intensity levels of the input image 150 may be presented as an output image 160. It can be seen from the output image 160 that the floor boundaries become more prominent due to the enhanced contrast between the floor and the shelves and the walls.

Due to the above contrast enhancement process, when the output image 160 is applied to the vision enhancement apparatus 130, not only the existence of important point is substantially perceivable to the vision impaired user 140 compared to the neighbouring points but also the more important the point is, the more perceivable the point is to the vision impaired user 140.

For example, a perceived image 170 may represent what the vision impaired user 140 perceives, which results from applying the output image 160 to the vision enhancement apparatus 130. The perceived image 170 clearly shows that the important features, i.e. the boundaries between the floor and the shelves and the walls, are perceivable to the vision impaired user 140.

An example method 200 for enhancing vision for a vision impaired user is described with reference to FIGS. 2, 3 and 4.

In this example, it is assumed that the resolution of the input image is the same as that of the vision enhancement apparatus 130 for easy description. In another example, the resolution of the input image may be higher than that of the vision enhancement apparatus 130, in which case the input image may be down-sampled to match the resolution of the vision enhancement apparatus 130.

Further, in this example, the visual intensity levels of the images are represented by grey levels of points of the images. In another example, the intensity levels of the images may also represented by RGB space or any other suitable way without departing from the scope of the present disclosure.

An input image 410 is shown in FIG. 4(a). It should be noted that only a portion of the input image 410 is shown for illustration purpose. This portion of the input image 410 is indicated by slide line boxes, each of which corresponds to a point of the input image 410. The portions of the input image 410 that are not shown are represented by the dash extend lines.

The portion of input image 410 comprise 3×3 points. A point in the portion of the input image 410 is denoted by the relative location of the point in the portion of the input image 410. For example, the point at the top-left corner of the portion is denoted as the point (1,1), and the point at the bottom-right corner of the portion is denoted as the point (3,3).

The intensity levels of the points of the input image 410 are represented by numbers in the corresponding box in the input image 410. For example, the intensity level of the point (2, 1) is 8 and the intensity level of the point (2, 2) is 4. These numbers are for the purpose of the illustrating the intensity levels of the points of the input image 410. That is, these numbers are not part of visual presentation of the input image 410.

The processing device 110, for each point in the input image 410, determines 210 a weight for the point based on visual importance of the point in the input image 410.

The weights for the points may be presented as an importance map 420 shown in FIG. 4(b). Each box of the importance map 420 spatially correspond to each point of the input image 410. For example, the weight for the point (2,2) is 0.9, and the weight for points other than the point (2,2) is 0.2. An example method of determining the importance map 420 is described in D. Feng and C. McCarthy. *Enhancing scene structure in prosthetic vision using iso-disparity contour perturbance maps*. Proceedings of the 2013 35th Annual International Conference of the IEEE Engineering in Medicine and Biology Society (EMBC), Osaka, Japan, pages 5283-5286. The importance map 420 may be determined in any other way without departing from the scope of the present disclosure.

The processing device 110 compares the weight for a point to a threshold in order to determine an output value for an imaging element of the vision enhancement apparatus 130 that corresponds to the point.

Specifically, the processing device 110 determines 220 if the weight for the point meets the threshold, which in this example means the weight for the point is at a level greater than the threshold where the point is considered to be an important point. In this example, the greater the weight for the point is, the more important the point is. In another example, the weight for the point may meet the threshold when the weight is less than the threshold without departing from the scope of the present disclosure, in which case the greater the weight for the point is, the less important the point is.

In this example, a greater intensity level may represent a higher brightness of a point. That is, the greater the intensity level of the point is, the brighter the point is. In other example, a greater intensity level may represent a lower brightness of a point without departing from the scope of the present disclosure, in which case the greater the intensity level of the point is, the darker the point is.

Further, in the context of the present disclosure, the terms "greater" or "less" are used to distinguish two variables that are not equal in their values and should not be understood to be a limitation to their values.

If the weight for the point meets the threshold, the processing device 110 determines 230 the output value so that a difference between first output value and an intensity level of the portion of the input image 410 neighbouring the point increases with the weight. It should be noted that the difference is at least one Just-Noticeable-Difference (JND) of the vision enhancement apparatus 130. This way, the contrast between the point and the neighbouring points is enhanced and when the output value is applied to the imaging element to create a visual stimulus, the visual stimulus is substantially perceivable by the vision impaired user 140 compared to visual stimuli created by the neighbouring imaging elements. It should be noted that the JND of a vision enhancement apparatus may be different depending on where the vision enhancement apparatus is implanted. For example, the JND of the subretinal implant 130 in the example shown in FIG. 13 may be different to that of an epiretinal implant.

On the other hand, if the weight for the point does not meet the threshold, the method 200 proceeds to the entry point A. The process 300 following the entry point A is shown in FIG. 3.

Figure 3:
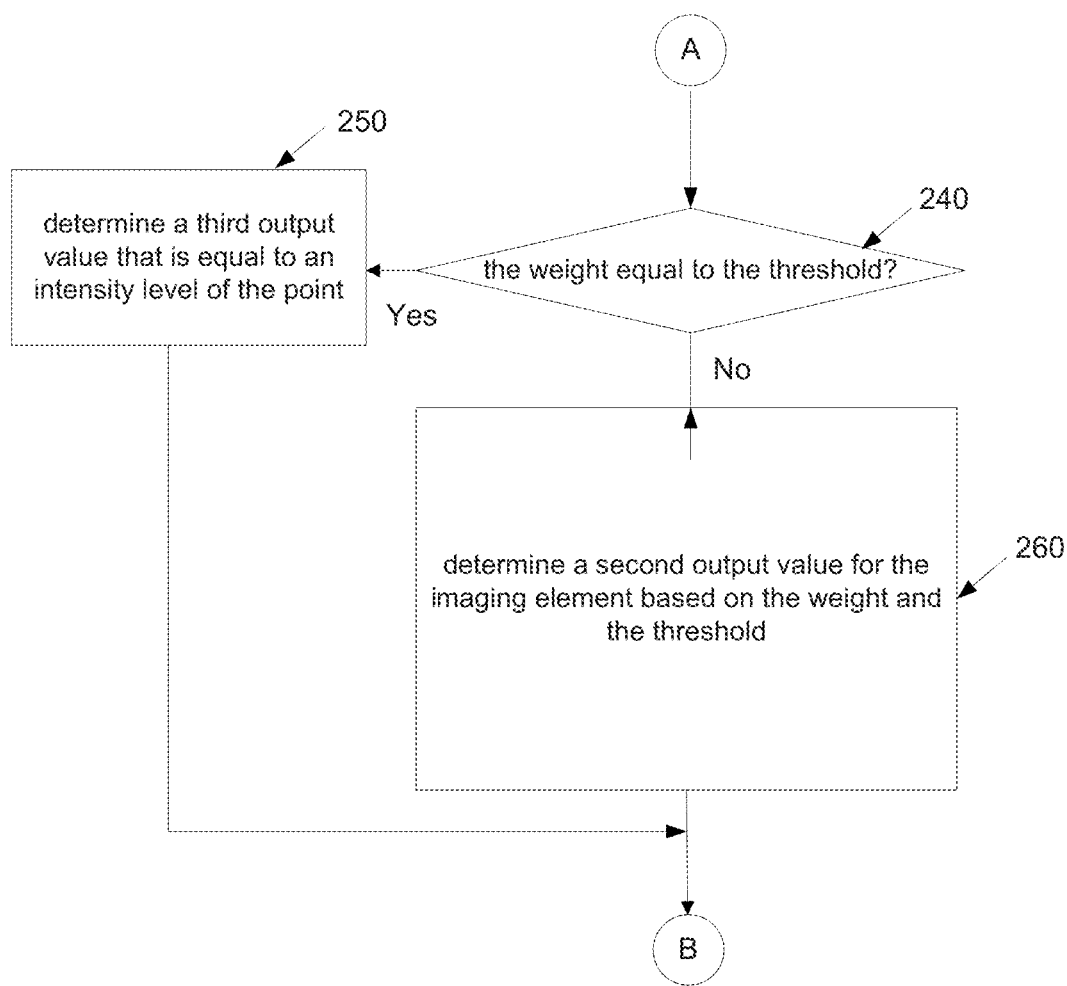
FIG. 3 shows an example method for enhancing vision for a vision impaired user according to the present disclosure.

As shown in FIG. 3, the processing device 110 further determines 240 if the weight for the point is equal to the threshold.

If the weight for the point is equal to the threshold, the output value is determined 250 to be an intensity level of the point.

On the other hand, if the weight for the point doesn't meet the threshold and is not equal to the threshold, which in this example means that the weight for the point is less than the threshold, the processing device 110 determines 260 the output value based on the weight for the point and the threshold, such that a difference between the output value and the intensity level of the portion of the input image 410 is less than a difference between the intensity level of the point and the intensity level of the portion of the input image 410. This way, the contrast between the point and the neighbouring point is attenuated and when the output value is applied to the imaging element to create a visual stimulus, the visual stimulus is less perceivable by the vision impaired user 140.

Figure 2:
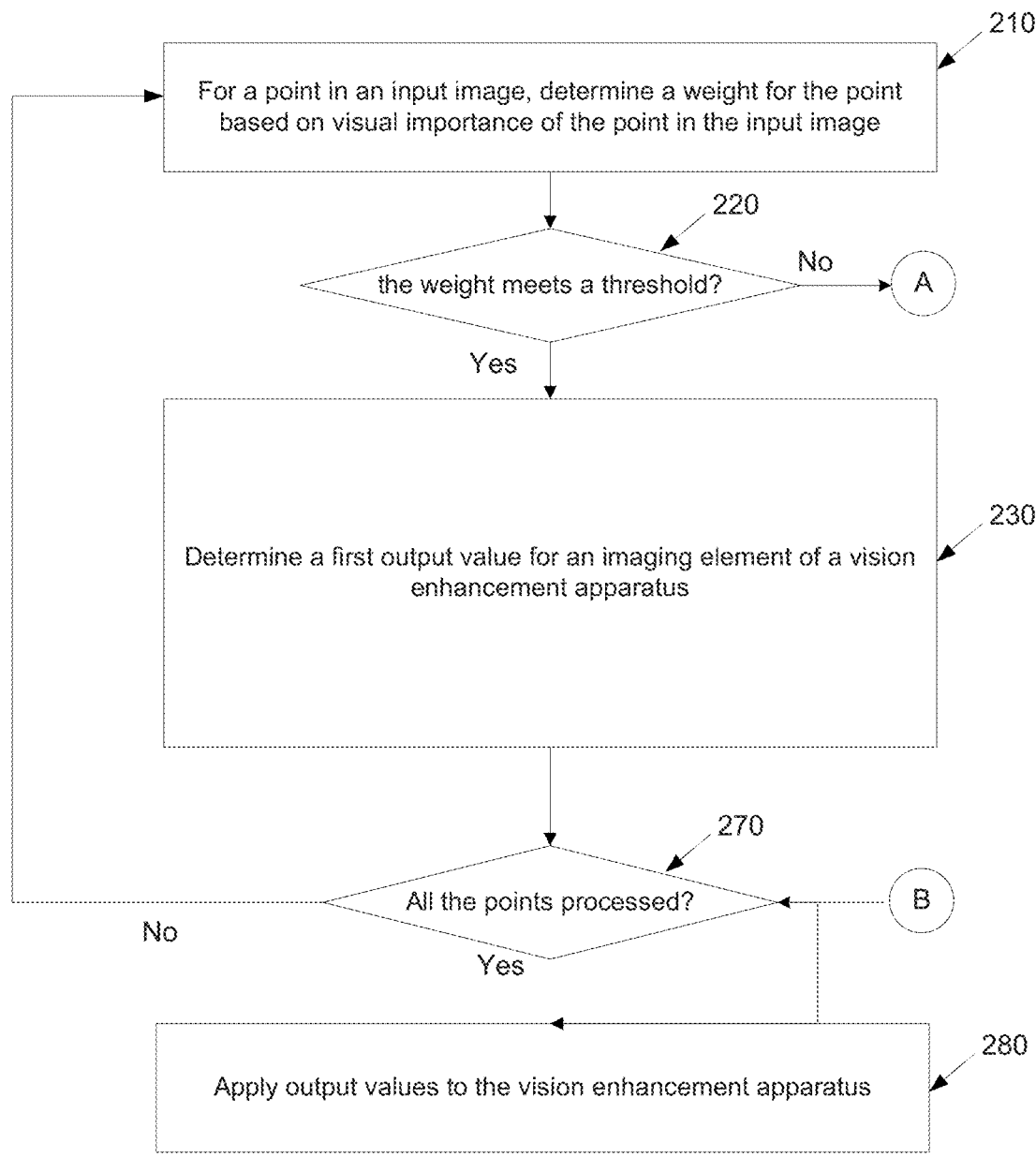
FIG. 2 shows an example method for enhancing vision for a vision impaired user according to the present disclosure.

The methods 200 proceeds to the entry point B to return to the process 200 shown in FIG. 2.

As shown in FIG. 2, having processed the point in the portion of the input image 410, the processing device 110 determines 270 if all the points in the input image 410 have been processed.

If not all the points in the input image 410 have been processed as above, the method 200 proceeds to process the next point in the portion of the input image 410 or the next portion of the input image 410. Otherwise, the processing device 110 may apply output values to the imaging elements of the vision enhancement apparatus 130.

In this example shown in FIG. 1, as the weight for the points other than the point (2,2) is 0.2, which is equal to the threshold 0.2, the output values for the imaging elements corresponding to those points are determined to be intensity levels of those points, as shown in an output image 420 shown in FIG. 4(c).

However, for the point (2,2), as the weight for this point is 0.9, which meets the importance threshold 0.2, the contrast between the point (2,2) and the intensity level of the portion of the input image 410 needs to be enhanced.

Specifically, the processing device 110 calculates an average intensity level of the neighbouring points to represent the intensity level of the portion of the input image 410. In this example, the neighbouring points comprises the point being processed. As a result, the average intensity level of neighbouring points is 5.

In another example, the neighbouring points may not comprise the point being processed. Further, measurements other than the average intensity level of neighbouring points may be used to represent the intensity level of the portion of the input image 410.

To determine the output value for the imaging element of the vision enhancement apparatus 130 corresponding to the point (2,2) in the portion of the input image 410, the processing device 110 may determine the Just-Noticeable-Difference of the vision enhancement apparatus 130 with reference to the average intensity level of the portion of the input image 410 based on the Weber-Fechner Law.

The Weber fraction needed in applying the Weber-Fechner Law is 0.4 in this example, and the minimum perceivable intensity level is 1. The Weber fraction and the minimum perceivable intensity level may depend on the physical characteristics of the vision enhancement apparatus 130. By applying the Web-Fechner Law, the JND with reference to the average intensity level of the portion of the input image 410 shown in FIG. 4 is 2.4.

Figure 5:
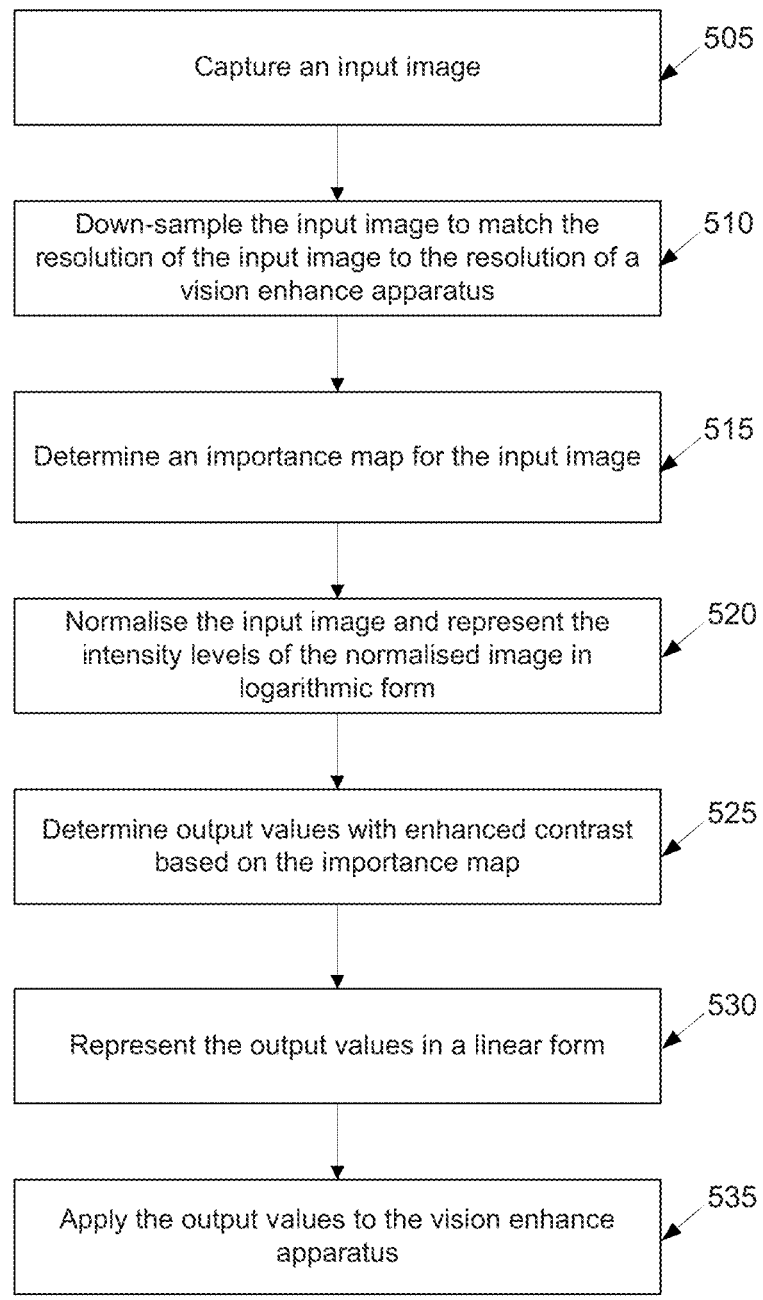
FIG. 5 shows an example method for enhancing vision for the vision impaired user according to the present disclosure.

Therefore, the difference between the output value for the point (2,2) and the intensity level of the portion of the input image 410 is the JND at a minimum. Further, the difference increases with the weight for the point (2,2), such that the more important the point is, the higher contrast between the point and neighbouring points is. The numerical relationship between the difference and the weight will be described with reference to the process 500 shown in FIG. 5.

In the example shown in FIG. 4, the difference between the output value for the point (2,2) and the intensity level of the portion of the input image 410 is for example 3.4, so the output value of the imaging element of the vision enhancement apparatus 130 is 8.4., as shown in the output image 430.

The output values for all the points in the portion of the input image 410 are applied to the vision enhancement apparatus 130 that is implanted behind the retina of the vision impaired user 140. The vision enhancement apparatus 130 translates the output values representing visual intensity levels into electric current or voltage signals and applies these electric signals to the imaging elements to stimulate the retina of the vision impaired user 140. As a result, the vision impaired user 140 may perceive the input image 410. A perception of the input image 410 may be shown as a perceived image 440 in FIG. 4(d).

An intensity level of a point in the perceived image 440 is represented by a symbol with a cap over a number. The number represents the output value that is applied to the imaging element corresponding to the point. It can be seen from the perceived image 440 that since the output value for the point (2,2) in the perceived image 440 is at least one JND more than the intensity level of the portion of the input image 410, the point (2,2) in the perceived image 440 is substantially perceivable to the vision impaired user 140 compared to neighbouring points in the perceived image 440. Specifically, the point (2,2) in the perceived image 440 is perceivable to the vision impaired user 140 in the sense that the point (2,2) in the perceived image 440 is distinguishable from the overall perception of the neighbouring points in the perceived image 440. An example method 500 for enhancing vision for the vision impaired user 140 is described with reference to FIG. 5.

The camera 120 may capture 505 an input image and sends the input image 505 to the processing device.

As the resolution of the input image captured by the camera 120 may be higher than the resolution of the vision enhancement apparatus 130, the processing device 110 down-samples 510 the input image to match the resolution of the input image to the resolution of the vision enhance apparatus 130. For example, the down-sampling of the input image makes the solution of the input image the same as that of the vision enhancement apparatus 130.

The processing device 110 determines 515 an importance map for the down-sample input image indicating the importance weight for each point in the down-sampled input image 160. Clearly, the resolution of the importance map matches the resolution of the vision enhancement apparatus 130.

It should be noted that the matching of the resolution of the input image and the importance map may also be performed in any other suitable way without departing from the scope of the present disclosure. For example, the matching can be achieved by the following process:

determining an importance map based on the input image having a higher resolution. As a result, the importance map has a higher resolution accordingly; and down-sample the input image and the importance map to match the resolution of the vision enhancement apparatus 130, respectively.

For easy description, the input image and the importance map matching the resolution of the vision enhancement 130 are denoted by I and S, respectively. The value range of a weight for a point in the importance map may be between 0 and 1. Further, the output image that is determined based on the importance map is denoted by I'.

The intensity level of a point in the output image I may be related to the intensity level of a point in the input image based on the process described in J.-S. Lee. *Digital image enhancement and noise filtering by use of local statistics.* Pattern Analysis and Machine Intelligence, IEEE Transactions on, (2):165-168, 1980. Specifically, $$I'_p = \mu_p + (1+\beta)(I_p + \mu_p) \tag{1}$$

where $I_p$ is normalised the intensity level of the point p from its intensity level, and $\mu_p$ is the mean of normalised intensity levels in a portion of the input image I in the neighbourhood of the point p. $\mu_p$ may be for example the average normalised intensity level of a local portion neighbouring the point p. The factor $\beta$ determines the aggressiveness of contrast adjustment. $I'_p$ is the normalised output value for the point p.

To maintain the same scaling throughout this process, the intensity level of the point p may be normalised 520.

As a logarithmic form of Equation (1) is adopted in this example, the intensity level of the point p may be normalised as follows:

$$I_p = 1 - \frac{I_{pl}}{I_{max}} \quad (2a)$$

wherein $I_{pl}$ is the original intensity level of the point p of the input image I, for example, represented by grey levels 0 to 255, and $I_{max}$ is the maximum allowable value in the dynamic range of the input image I. It can be seen from Equation (2a) that $I_p$ is between 0 and 1. Further, $\mu_p$ may be normalised in a similar way.

In another example, if the intensity level of the point p is used in a linear form, the intensity level of the point p may be normalised as follows:

$$I_p = \frac{I_{pl}}{I_{max}} \quad (2b)$$

As described in G. Deng, L. Cahill, and G. Tobin. *The study of logarithmic processing model and its application to image enhancement.* IEEE Transactions on image processing, 4(4):506-512, 1994., the logarithmic image processing (LIP) form of the Equation (1) is adopted in this example to provide a better characterisation of saturation and other properties of the human vision system, see K. Panetta, S. Agaian, Y. Zhou, and E. J. Wharton. *Parameterized logarithmic framework for image enhancement.* Systems, Man, and Cybernetics, Part B: Cybernetics, IEEE Transactions on, 41(2):460-473, 2011 and J. -C. Pinoli. *The logarithmic image processing model: Connections with human brightness perception and contrast estimators.* Journal of Mathematical Imaging and Vision, 7(4):341-358, 1997.

Thus, Equation (1) becomes:

$$\log(I'_p) = \log(\bar{\mu}_p) + (1+\beta)(\log(I_p) - \log(\bar{\mu}_p)) \quad (3)$$

wherein $I'_p$, $I_p$, $\bar{\mu}_p$ are the logarithmic forms of $I'_p$, $I_p$, $\mu_p$, respectively.

In the present disclosure, the second term the above Equation (3) may be replaced with a contrast adjust function:

$$\log(I'_p) = \log(\bar{\mu}_p) + \text{sign}(\Delta_I)\Delta_p \quad (4)$$

where $\Delta_p$ defines the difference between the output value for the point p and intensity of the portion of the input image I, i.e., the extent of desired contrast change. The output value for the imaging element corresponding to the point p may be determined 525 based on the above Equation (4).

Specifically, $$\Delta_p = \begin{cases} \max(|\log(1 - S_p^\gamma)|, |\Delta_I|) & \text{if } S_p > s_t \\ \max(|\Delta_I| - \Delta_s, 0) & \text{otherwise} \end{cases} \quad (5)$$

and:

$$\Delta_I = \log(I_p) - \log(\bar{\mu}_p) \quad (6)$$

$$\Delta_s = \log(1 - s_t^\gamma) - \log(1 - S_p^\gamma) \quad (7)$$

It can be seen from the above equations, for a point of the portion of the input image I having a weight $S_p > s_t$, which means the weight for the point p meets the threshold $s_t$, the difference between the output value for the point p and the intensity level of the portion of the input image I exponentially increases with the weight. That is, the contrast increases the weight.

It should be noted that if a sufficient difference already exists between the intensity level of the point p and the intensity level of the portion of the input image I, for example, if the difference already is greater than at least one JND of the vision enhancement apparatus with reference to the intensity level of the portion of the input image I, the output value may be determined to be the intensity level of the point p.

On the other hand, if for $S_p < s_t$, the contrast is reduced. Specifically, the output value for the imaging element is determined based on the weight and the threshold, such that a difference between the output value and the intensity level of the portion of the input image I is less than a difference between the intensity level of the point p and the intensity level of the portion of the input image I, such that when the second output value is applied to the imaging element to create a visual stimulus, the visual stimulus is less perceivable by the vision impaired user 140.

The term, $\text{sign}(\Delta_I)$ in Equation (4), ensures contrast adjustments follow the existing intensity level difference direction. Specifically, if an intensity level of the point p is greater than the intensity level of the portion of the input image I, the output value is greater than the intensity level of the portion of the input image I; if the intensity level of the point p is less than the intensity level of the portion of the input image I, the output value is less than the intensity level of the portion of the input image I.

Further, for $S_p > s_t$, if the intensity level of the point p is equal to the intensity level of the portion of the input image I, the output value may be either greater or less than the intensity level of the portion of the input image I such that the difference between the output value and the intensity level of the portion of the input image I is at least one Just-Noticeable-Difference of the vision enhancement apparatus 130. However, if the intensity level of the point p and the intensity level of the portion of the input image I are both at the maximum intensity level that can be applied to the vision enhancement apparatus 130, the output value determined may be less than the maximum intensity level.

On the other hand, for $S_p < s_t$, if the intensity level of the point p is equal to the intensity level of the portion of the input image I, as the difference between the intensity level of the point p and the intensity level of the portion of the input image I is zero in this case, the output value may be determined to be the intensity level of the point since the contrast may not be reduced further.

The factor $\beta$ in Equation (2) is replaced with a parameter $\gamma$ in Equation (6). The parameter $\gamma$ depends on a model of human contrast perception that is particular to the vision enhancement apparatus 130.

For the case that $S_p > s_t$, the desired change to contrast is achieved by a power law which follows the model of perceived contrast and physical contrast in human perception, above low luminance as described in E. Peli, J. Yang, R. Goldstein, and A. Reeves. *Effect of luminance on suprathreshold contrast perception.* Journal of the Optical Society of America A, 8(8):1352-1359, 1991., hence the parameter is exponential with respect to the average intensity level of the portion of the input image I.

The Weber-Fechner Law is applied in this disclose to determine the required change to the input stimulus required to achieve a JND in the perceptual response. The law takes into account the psychophysically observed property that the threshold for perceiving a JND, δ', increases with the stimulus magnitude, as described in S. Ferradans, M. Bertalmio, E. Provenzi, and V. Caselles. *An analysis of visual adaptation and contrast perception for tone mapping.* Pattern Analysis and Machine Intelligence, IEEE Transactions on, 33(10):2002-2012, 2011:

$$\delta' = K_w(V_o + V) \qquad (8)$$

where V is the instantaneous input stimulus, and $V_o$ is a threshold input stimulus for a lowest perceivable response. $K_w$ is the empirically determined Weber fraction, which determines the sensitivity to response changes in a specific human viewer.

Therefore, the Weber-Fechner Law may be applied to the present disclosure to ensure perceivability of contrast adjustments from the average intensity level of the portion of the input image I. Particularly, $$\delta' = K_w(\mu_p + d_0) \qquad (9)$$

where $d_0$ is the minimum output value that can create a perceivable stimulus when applied to the vision enhancement apparatus 130.

Given the JND, δ', γ may be solved as follows:

$$s_t^\gamma = \delta' \qquad (10)$$

from which γ may be obtained:

$$\gamma = \frac{\log(\delta')}{\log(s_t)} \qquad (11)$$

Thus, for a given average intensity level of a portion of the input image I, $\mu_p$, and the importance weight for the point p, $S_p$, the resulting contrast adjustment objective, $S_p^\gamma$, in Equation (5) is greater than the JND, δ', and exponentially increases with the importance weight for the point p, $S_p$, for all points having the weight $S_p > s_t$.

Since $\Delta_p$ in Equation (5) is the logarithmic form of $S_p^\gamma$, $\Delta_p$ increases with the importance weight for the point p, $S_p$ accordingly.

It can be seen that the output value $\bar{I}'_p$ determined from Equation (4) is in the logarithmic form and is normalised. Therefore, to represent 530 the output value $\bar{I}'_p$ in the dynamic range of the original input image I, for example, representing the output value $\bar{I}'_p$ in grey levels 0 to 255, the output value $\bar{I}'_p$ may be transformed as follows:

$$I'_{pl} = 1 - \exp(\log(\bar{I}'_p)) \qquad (12)$$

It can be seen from Equations (4), (5) and (7), if $S_p = s_t$, the output value $\bar{I}'_p$ is equal to the intensity level $I_p$ of the point p, which means the contrast between the point p and the portion of the input image I may not change.

After all the points are processed as above, the output values for the imaging elements may be applied 535 to the vision enhancement apparatus 130 to create stimuli for a perception of the important features in the input image I.

Figure 6:
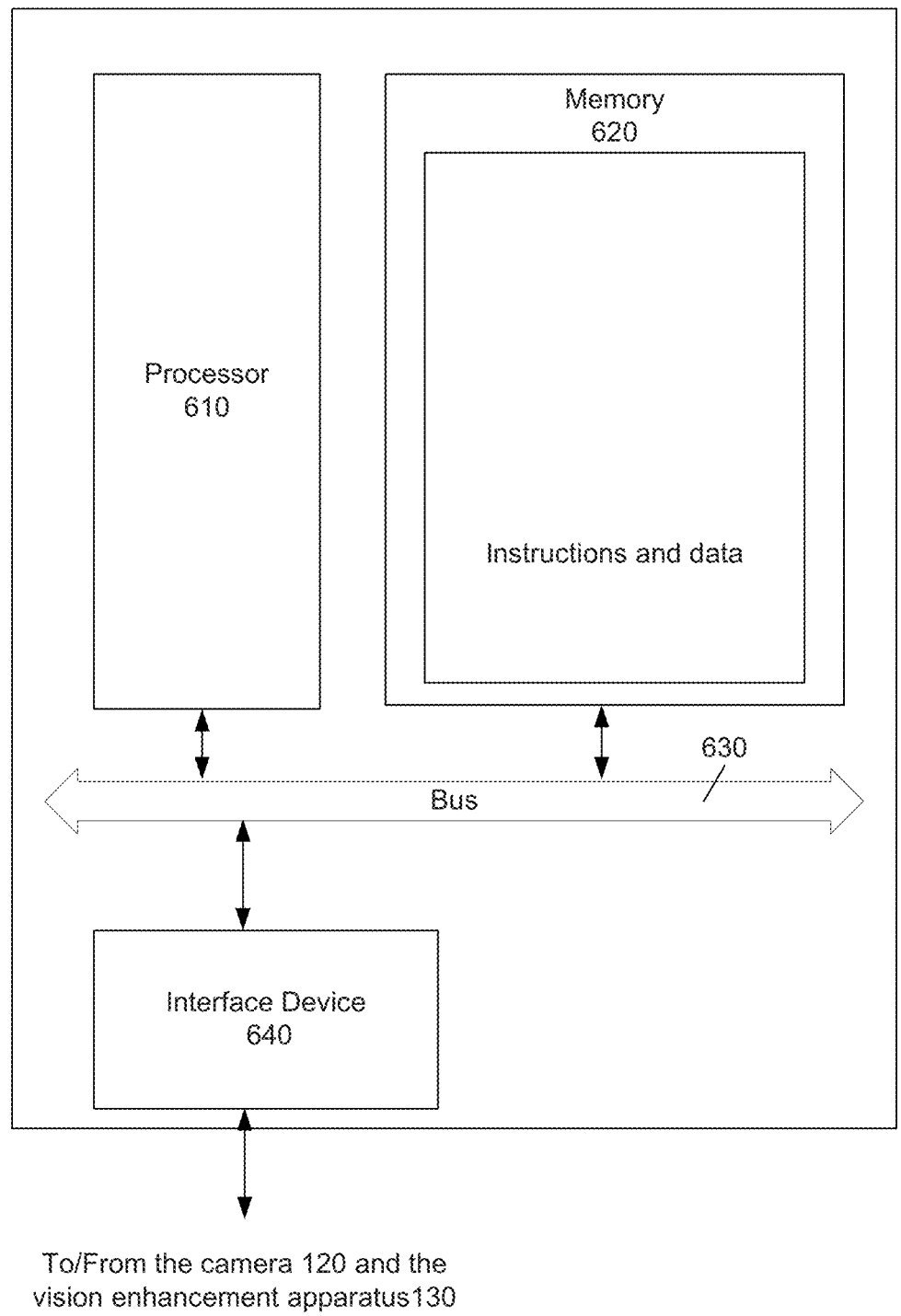
FIG. 6 shows an example processing device according to present disclosure.

FIG. 6 illustrates an example processing device 110 according to present disclosure.

The processing device 110 includes a processor 610, a memory 620 and an one or more interface devices 640 that communicate with each other via a bus 630. The memory 620 stores instructions and data for the methods and processes described above, and the processor 610 performs the instructions from the memory 620 to implement the methods and processes. It should be noted that although the processing device 110 is shown as an independent element in FIG. 1, the processing device 110 may also be part of another element for example the camera 120.

The processor 610 may be, for example, a general-purpose central processing unit (CPU). The processor 610 may also be any other types of processor capable of performing the above instructions without departing from the scope of the present disclosure, for example, a field-programmable gate array (FPGA), an application-specific integrated circuit (ASIC), etc.

The memory 620 includes a suitable computer readable medium, for example, random access memory (RAM), read-only memory (ROM), an optic disk, or a high-speed disk or disk array. The computer readable media may also include carrier waves and transmission media. Example carrier waves may take the form of electrical, electromagnetic or optical signals conveying digital data streams along a local network or a publically accessible network such as the Internet.

The bus 630 is a circuit that communicates data and instructions among the processor 610, the memory 620 and the one or more interface devices 640. Part of the bus 630 may be used to connect the process 610 and the memory 620. Part of the bus 630 may be used to connect to the one or more interface devices 640 to communicate data and instructions with the camera 120 and/or the vision enhancement apparatus 130. The bus 630 may operate according to bus protocols, for example, Industry Standard Architecture (ISA), or Peripheral Component Interconnect (PCI). The bus 630 may be organised in other forms or operate according to different industry standards without departing from the scope of the present disclosure.

The one or more interface devices 640 may include a wireline interface or a wireless interface that receives the input image 150 from the camera 120 and apply the intensity levels of the points of the output image 160 to the vision enhancement apparatus 130. Particularly, the one or more interface devices 640 may include a serial interface (for example, RS-232, USB), a parallel interface (for example, DB-25), a high-definition multimedia interface (HDMI), a FireWire interface, an Ethernet interface, a WIFI interface or other suitable interfaces without departing from the scope of the present disclosure.

The processor 610 may perform the instructions from the memory 620
for a point in an input image, to determine a weight for the point based on visual importance of the point in the input image;
to compare the weight for the point to a threshold; and
if the weight for the point meets the threshold, to determine a first output value for an imaging element of a vision enhancement apparatus so that a difference between the first output value and an intensity level of a portion of the input image neighbouring the point increases with the weight,
wherein the difference is at least one Just-Noticeable-Difference of the vision enhancement apparatus, such that when the first output value is applied to the imaging element of the vision enhancement apparatus to create a first visual stimulus, the first visual stimulus is substantially perceivable by the vision impaired user.

The processor 610 may also perform other methods and processes described above with reference to the accompanying drawings.

Validation

Figure 7:
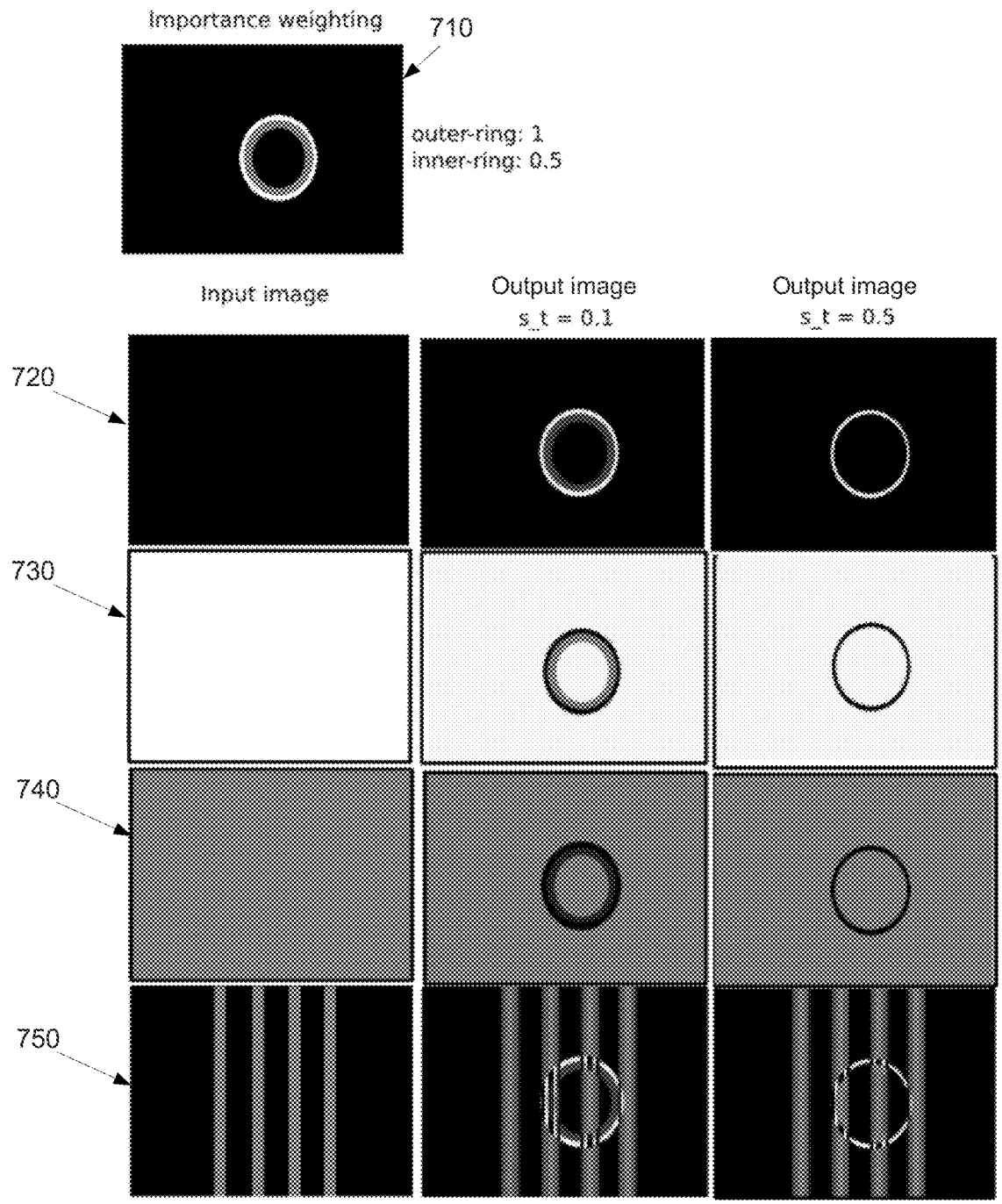
FIG. 7 illustrates an example of contrast adjustment according to the present disclosure.

FIG. 7 illustrates an example of contrast adjustment according to the present disclosure according to validate the method.

In FIG. 7, an importance map 710 including two concentric rings may be determined.

For the purpose of illustrating the method, the importance map 710 may be pre-determined regardless of an input image.

In the importance may 710, the importance weight $S_p$ for the outer ring is 1, and the importance weight $S_p$ for the inner ring is 0.5. All other importance weights are set to zero.

The method described above is applied to each of input images 720, 730, 740 and 750, which are given in the left column of FIG. 7, with reference to the importance map 710.

In this example, a 15×15 local averaging window is used, the Weber fraction $K_w$=0.08 and the output dynamic range is set to 8 brightness levels.

The resulting output images corresponding to the input images 720, 730, 740 and 750 for threshold $s_t$=0.1 and $s_t$=0.5 are given in the middle and right columns of FIG. 7.

The input images 720, 730 and 740 contain no contrast as all the points in each of these input images 720, 730 and 740 are at a same intensity level. The resulting output images, however, contain noticeable contrast change in accordance with the importance map 710 and the corresponding threshold.

Note that $s_t$=0.5 allows no contrast to result from the $S_p$=0.5 importance ring, which means when the importance weight of a point is equal to the threshold, the output value for the point value is equal to the intensity level of the point. That is, the contrast between the point p and the portion of the input image I may not change.

The output images corresponding to the input images 720, 730 also indicate the symmetry of contrast changes when the input image is uniformly black or white.

Figure 8:
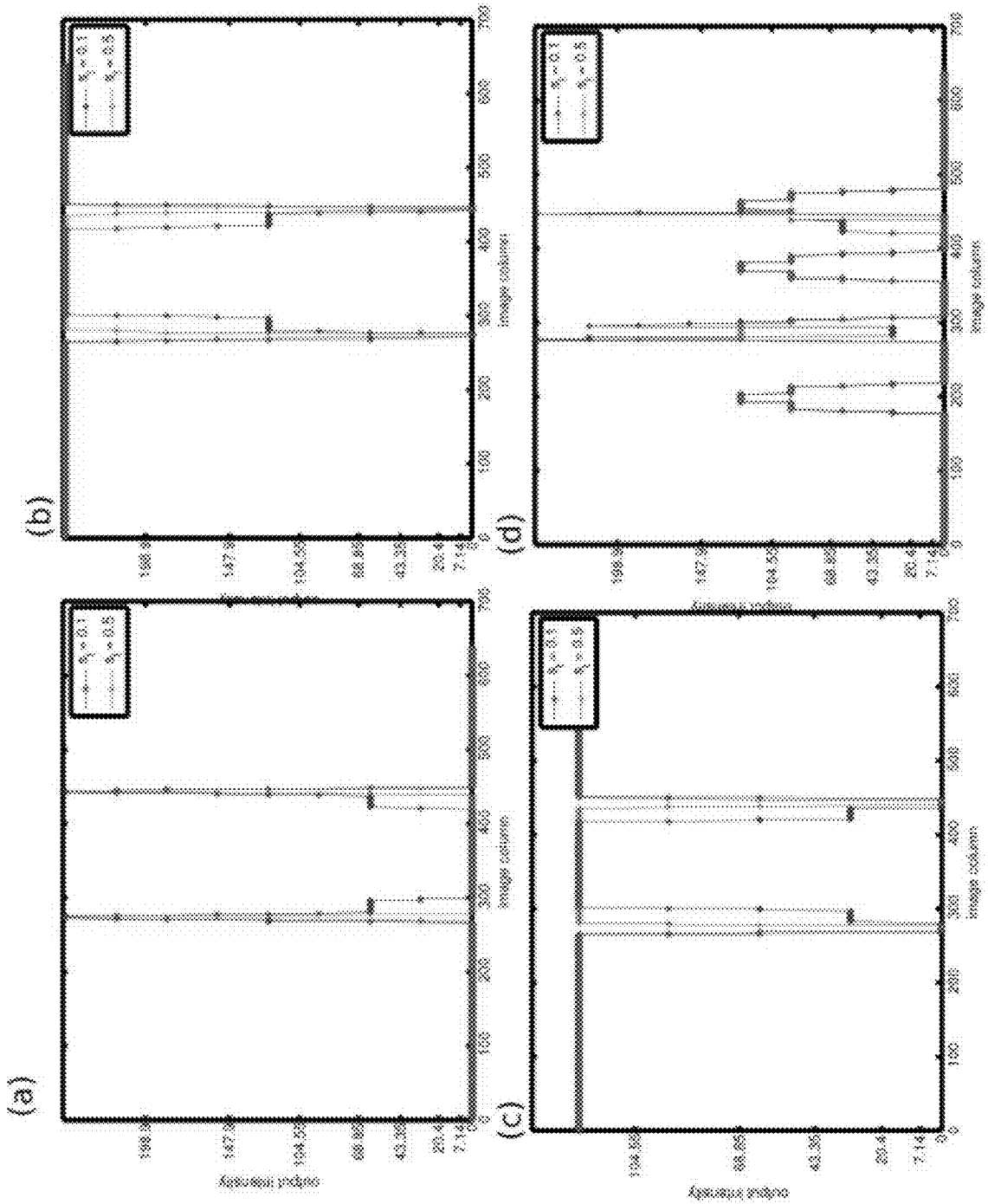
FIG. 8 illustrates plots comparing contrast adjustments for importance maps with respect to FIG. 7.

Corresponding plots of contrast adjustments across the middle row of each output image are given in FIGS. 8(a) to 8(c), numerically showing the visual contrast changes visualised in the output images in FIG. 7.

The output images corresponding to the input image 750 shows the resulting contrast changes in the presence of a uniformly grey striped pattern. As above, $s_t$=0.1 allows large contrast changes to occur at all points where non-zero importance weights exist. Given the low threshold, contrast changes generally result in an increase on existing contrast.

It is also shown that less contrast changes result from the $S_p$=0.5 ring. For $s_t$=0.5, only the outer ring produces a noticeable contrast change in the image. FIG. 8(d) also shows these results in plots of intensity across the middle row of both output images corresponding to the input image 750.

Evaluation with Simulated Prosthetic Vision

The method according to present disclosure may apply to prosthetic vision by using simulated prosthetic vision. Simulated prosthetic vision (SPV) aims to approximate the visual perception experienced by implanted patients, allowing for testing of vision processing strategies to occur with normal sighted persons. Simulation models commonly represent phosphenes as 2D Gaussians, with brightness and extent determined by the sampled intensity value, as described in S. C. Chen, G. J. Suaning, J. W. Morley, and N. H. Lovell. *Simulating prosthetic vision: I. Visual models of phosphenes*. Vision Research, 2009.

While not a complete representation of the true perceptual experience, the SPV provides a reasonable approximation to reported perception in clinical trials, see D. Nanduri, M. Humayun, R. Greenberg, M. McMahon, and J. Weiland. *Retinal prosthesis phosphene shape analysis*. In Engineering in Medicine and Biology Society, 2008. EMBS 2008. 30th Annual International Conference of the IEEE, pages 1785-1788. IEEE, 2008. [30, 22], and R. Wilke, V.-P. Gabel, H. Sachs, K.-U. B. Schmidt, F. Gekeler, D. Besch, P. Szurman, A. Stett, B. Wilhelm, T. Peters, et al. *Spatial resolution and perception of patterns mediated by a subretinal 16-electrode array in patients blinded by hereditary retinal dystrophies*. Investigative ophthalmology & visual science, 52(8):5995-6003, 2011.

SPV provides a useful platform for evaluating and developing plausible image enhancement strategies without the need for patients, and without bias to a particular device design.

Scene Structure Enhancement

A real-time depth-saliency algorithm is described in D. Feng and C. McCarthy. *Enhancing scene structure in prosthetic vision using iso-disparity contour perturbance maps*. In IEEE EMBC 2013. IEEE, 2013. in press, which is designed to detect regions of structural change in a depth image (obtained either from stereo algorithms or consumer RGB-D cameras). The algorithm applies a multi-scale sliding window, comparing histograms of depth gradient direction with surrounding regions to determine the uniqueness of the local gradient. The result is referred to as perturbance map, indicating the extent of structural change relative to local surrounding regions.

FIGS. 9(b) and 11(b) shows example output, i.e., the perturbance map or importance map, for each corresponding input image FIGS. 9(a) and 11(a), respectively.

The method according to the present disclosure may be run over captured RGB-D image sequences, with the contrast enhancement performed on single channel intensity images and importance maps determined directly from the depth-saliency algorithm output. The method is applied with a 15×15 local mean intensity window and $K_w$=0.08.

For comparison purposes, results for histogram equalisation and the logarithmic image processing (LIP) local adaptive methods defined in Equation (3), as described in G. Deng, L. Cahill, and G. Tobin. *The study of logarithmic image processing model and its application to image enhancement*. IEEE transactions on image processing, 4(4): 506-512, 1994, are also provided.

FIGS. 9(c) to (e) and 11(c) to (e) show the resulting images for all methods under comparison at full resolution, with 8 brightness levels. FIGS. 9(e) to (h) and 11(e) to (h) show corresponding SPV renderings for each method over a range of resolutions (the number of phosphenes) and dynamic ranges (the number of perceivable brightness levels).

Figure 9:
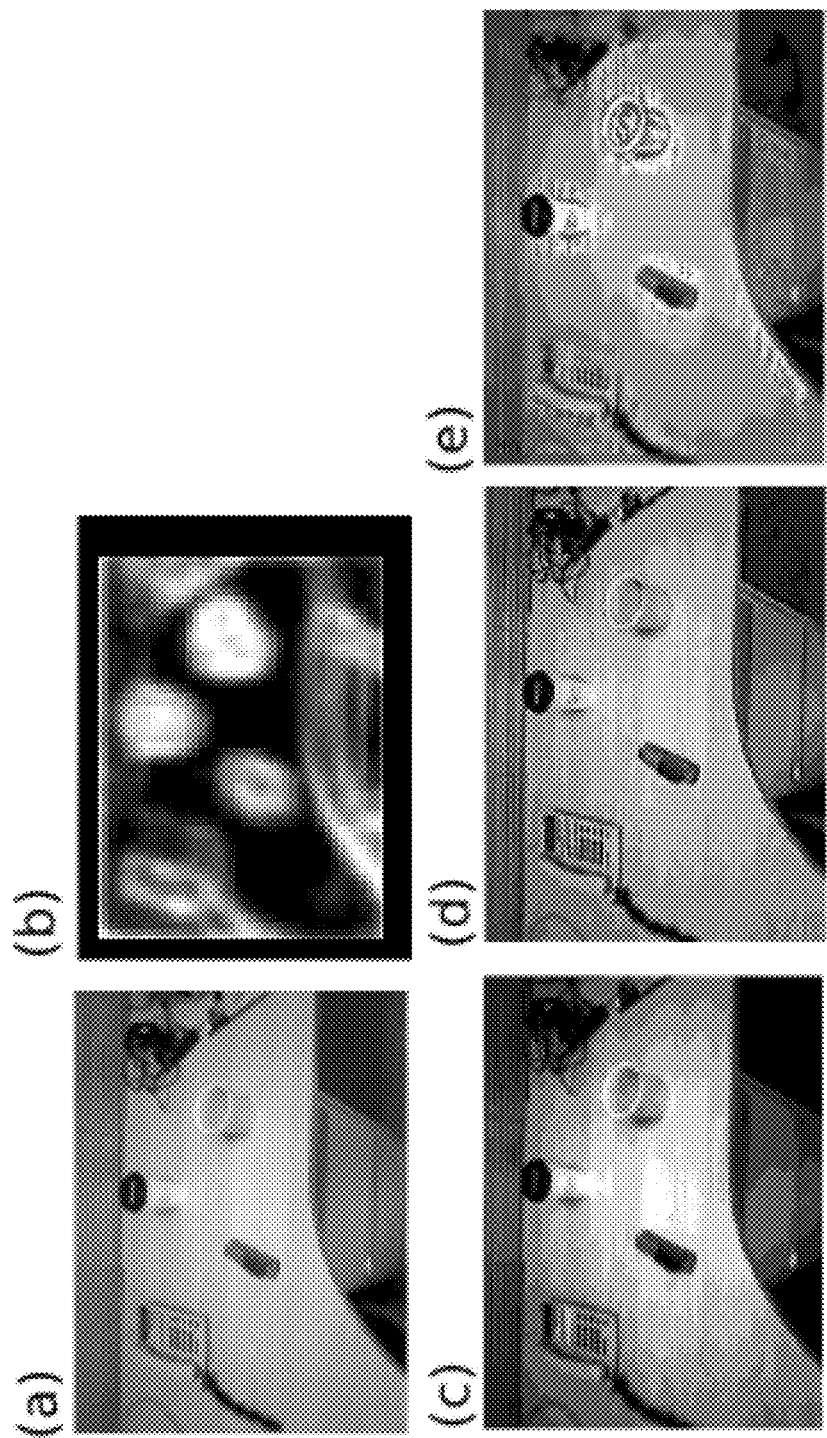
FIG. 9 illustrates an example comparison between the method according to the present disclosure and other methods.
Figure 9:
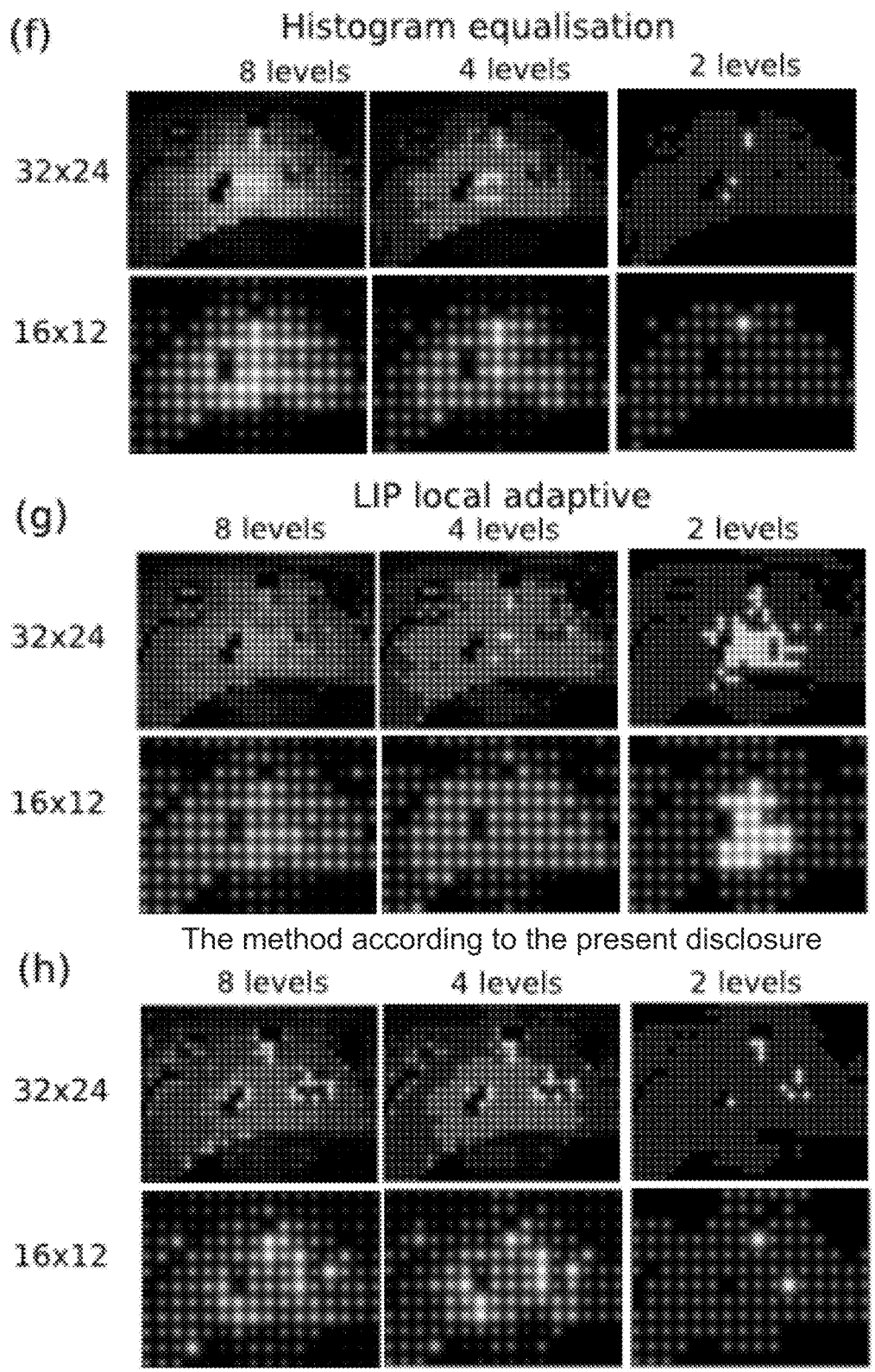

Results in FIG. 9 show a clearer visualisation of the lower contrast white objects on the light grey table-top surface using the method according to the present disclosure. In particular, the two white cups which are given high importance via the perturbance map are detectable. At the most diminished display settings (16×12 with 2 brightness levels), the cups and stapler remain perceivable. While both histogram equalisation and local adaptive methods retain some detail, the distinction between the table and objects appears comparatively worse at all corresponding display settings.

Figure 10:
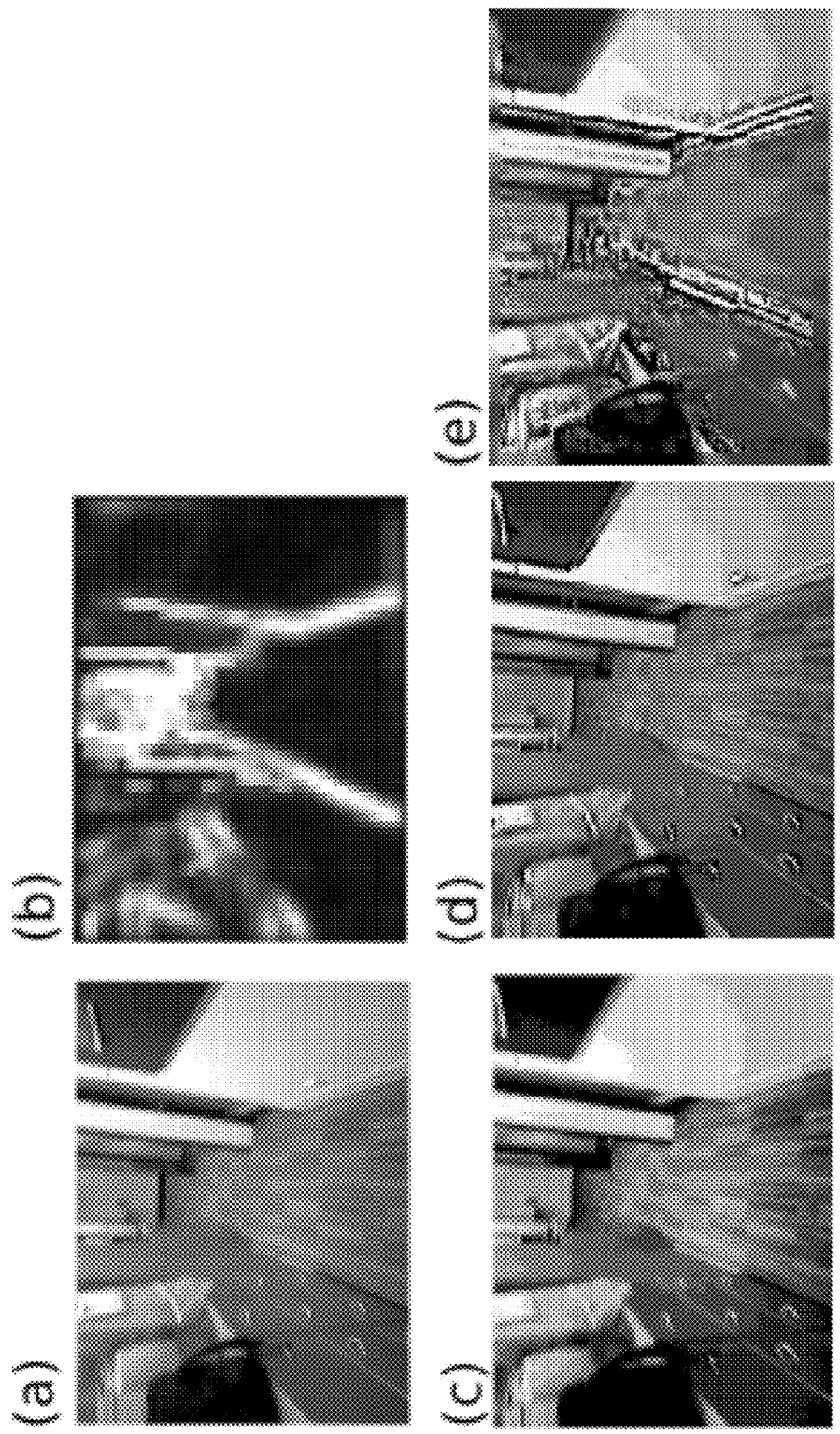
FIG. 10 illustrates an example comparison between the method according to the present disclosure and other methods.
Figure 10:
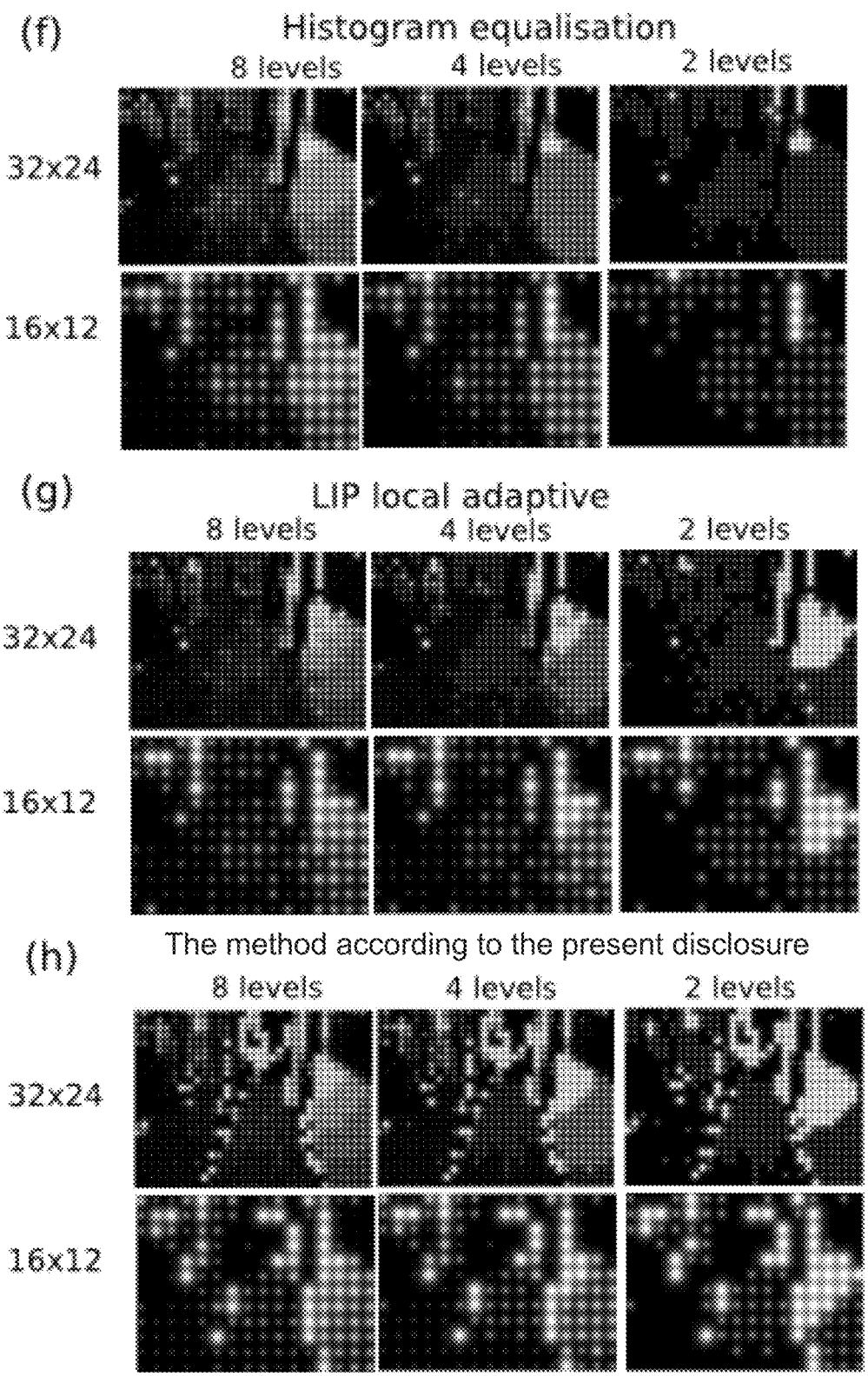
Figure 11:
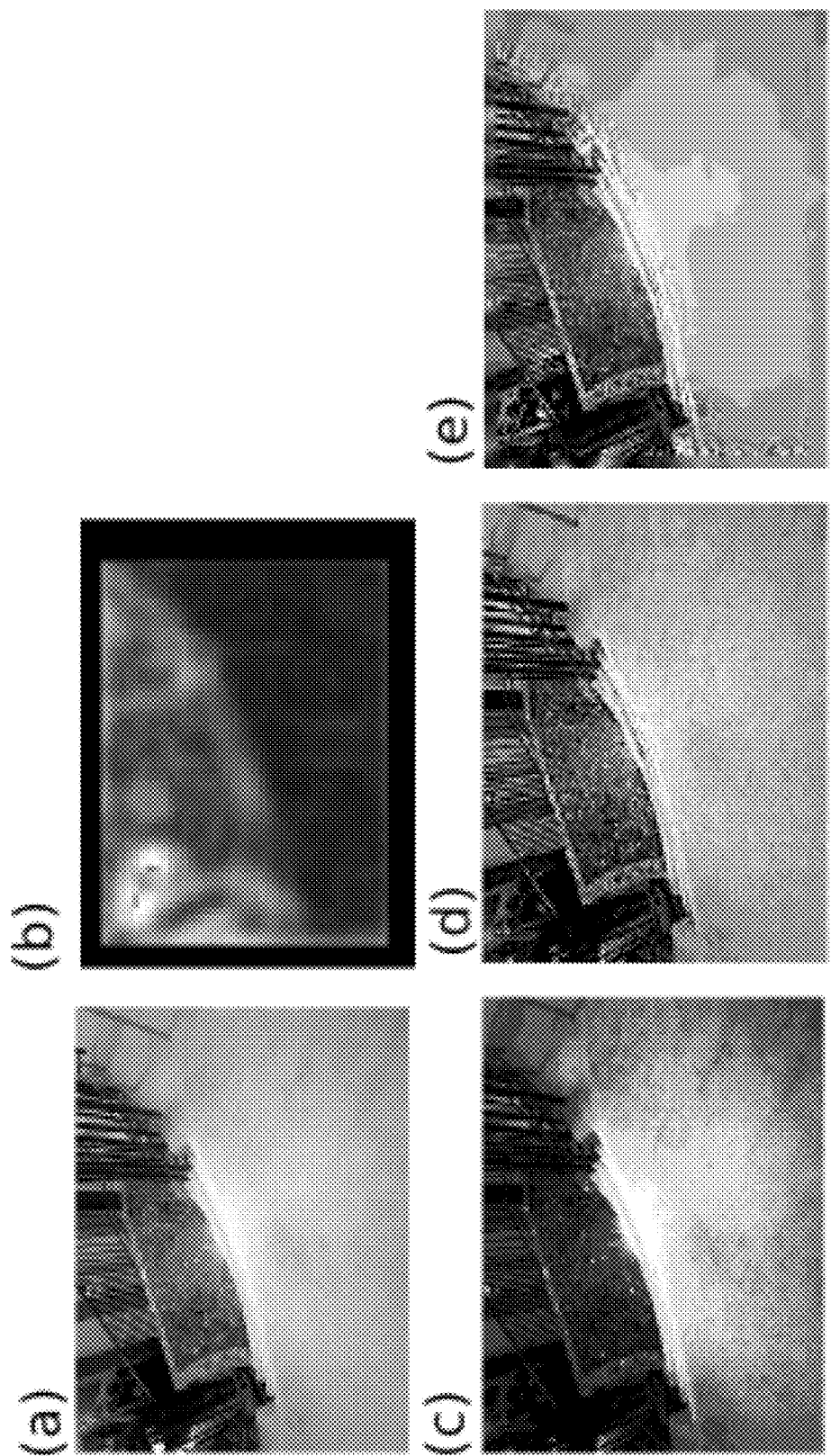
FIG. 11 illustrates an example comparison between the method according to the present disclosure and other methods.
Figure 11:
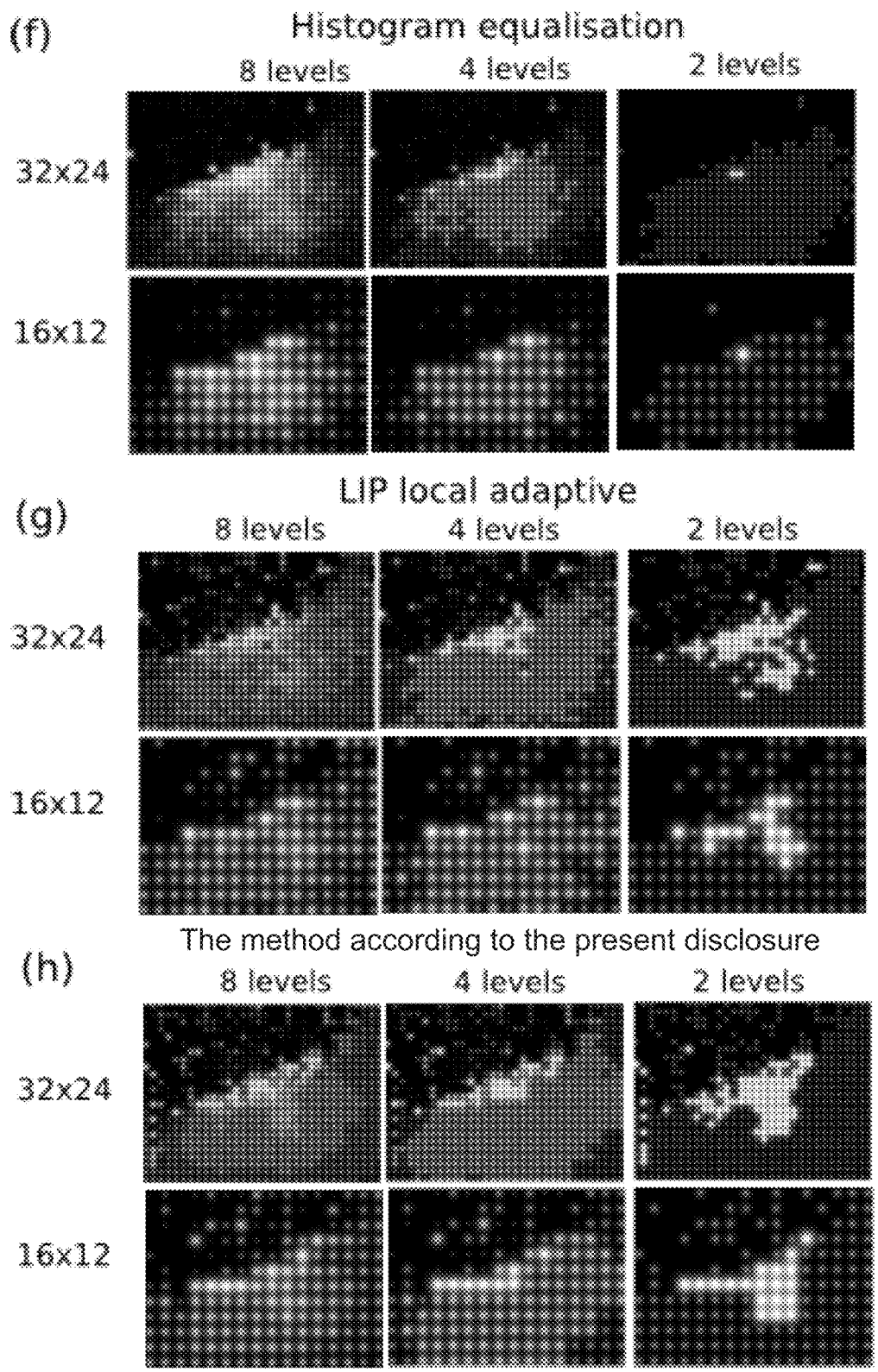

FIGS. 10 and 11 show examples of the augmentation in the navigation context. In both cases, histogram equalisation does a reasonable job of enhancing structural change where there is pre-existing contrast given sufficient dynamic range. However, the method according to the present disclosure provides a clearer delineation of key structural features such as the wall-floor boundaries in FIG. 11, and the precise drop-off point of the staircase in FIG. 12; at low dynamic range in particular. Note that in the latter case the most prominent contrast change marking the staircase drop-off in the original and histogram equalised images occurs three steps down, thus missing the crucial boundary between floor and staircase.

Quantitative Evaluation

To provide an objective measure of contrast enhancements, the measure of enhancement by entropy (EMEE) is applied, as described in S. S. Agaian, K. Panetta, and A. M. Grigoryan. *A new measure of image enhancement*. In IAS-TED International Conference on Signal Processing & Communication, pages 19-22. Citeseer, 2000:

$$EMEE(e) = -\frac{1}{k_1 k_2} \sum_{m=1}^{k_1} \sum_{l=1}^{k_2} \alpha(X)^\alpha \log(X) \text{ where} \quad (13)$$

$$X = \frac{I_{max}^{l,m}}{I_{min}^{l,m}}.$$

It should be noted that a small offset may be added to intensity values to avoid divide-by-zero error.

This metric is applied as this metric is generally accepted and proven effective as a human vision based metric of enhancement.

For our comparison, $\alpha=1$ and $k_1$, $k_2=16$. Table 1 below reports EMEE results for each method over full resolution (8 levels) images shown in FIGS. 9 to 11.

TABLE 1

EMEE results for 16 × 16 block regions above and below the importance threshold $s_t$.

| scene | orig | | hist eq | | local adaptive | | proposed | |
|---|---|---|---|---|---|---|---|---|
| | $>s_t$ | $\leq s_t$ | $>s_t$ | $\leq s_t$ | $>s_t$ | $\leq s_t$ | $>s_t$ | $\leq s_t$ |
| tabletop | 0.62 | 0.33 | 0.83 | 0.36 | 1.38 | 0.55 | 2.18 | 0.87 |
| office | 0.86 | 0.38 | 1.41 | 0.61 | 1.97 | 0.84 | 3.19 | 0.50 |
| dropoff | 1.02 | 0.34 | 0.89 | 0.27 | 1.58 | 0.48 | 1.11 | 0.38 |

To assess the effectiveness of the method according to the present disclosure to enhancement contrast in important regions, and attenuate contrast in less important regions, EMEE results computed for image blocks with mean importance above the threshold $S_t$, and for blocks below the threshold are shown.

EMEE results generally reflect the qualitative assessment above. The method according to the present disclosure achieves the highest EMEE score for above importance threshold regions in two of the three images. The local adaptive method achieves a slightly higher EMEE score for the dropoff scene, however, as noted earlier, FIG. 11 shows that the method according to the present disclosure provides a more precise demarcation of the actual drop-off location (particularly as dynamic range drops).

For regions below the importance threshold, Table 1 shows a substantial reduction in EMEE scores for the proposed method, indicating the attenuation of contrast away from important regions.

It should be noted that such metrics provide guidance only. User studies in the context of real environments may also be used to assess the true effectiveness of the method according to the present disclosure.

Looming Object Enhancement

To further demonstrate the generality of the method according to the present disclosure, the method is applied to an image sequence with corresponding time-to-contact maps providing for each pixel, a relative estimate of time before impact (up to scale) with surfaces in the scene.

Time-to-contact may be inferred from diverging optical flow patterns, as described in J. Koenderink and A. V. Doom. *Invariant properties of the motion parallax field due to the movement of rigid bodies relative to an observer*. Optica Acta, 22(9):773-791, 1975, and plays an important role in visuomotor control in a number of biological vision systems, including human vision, see M. Lappe. *Building blocks for time-to-contact estimation by the brain*. In H. Hecht and G. Savelsbergh, editors, Time-to-contact, Advances in Psychology. Elsevier, Amsterdam, The Netherlands, 2004.

Figure 12:
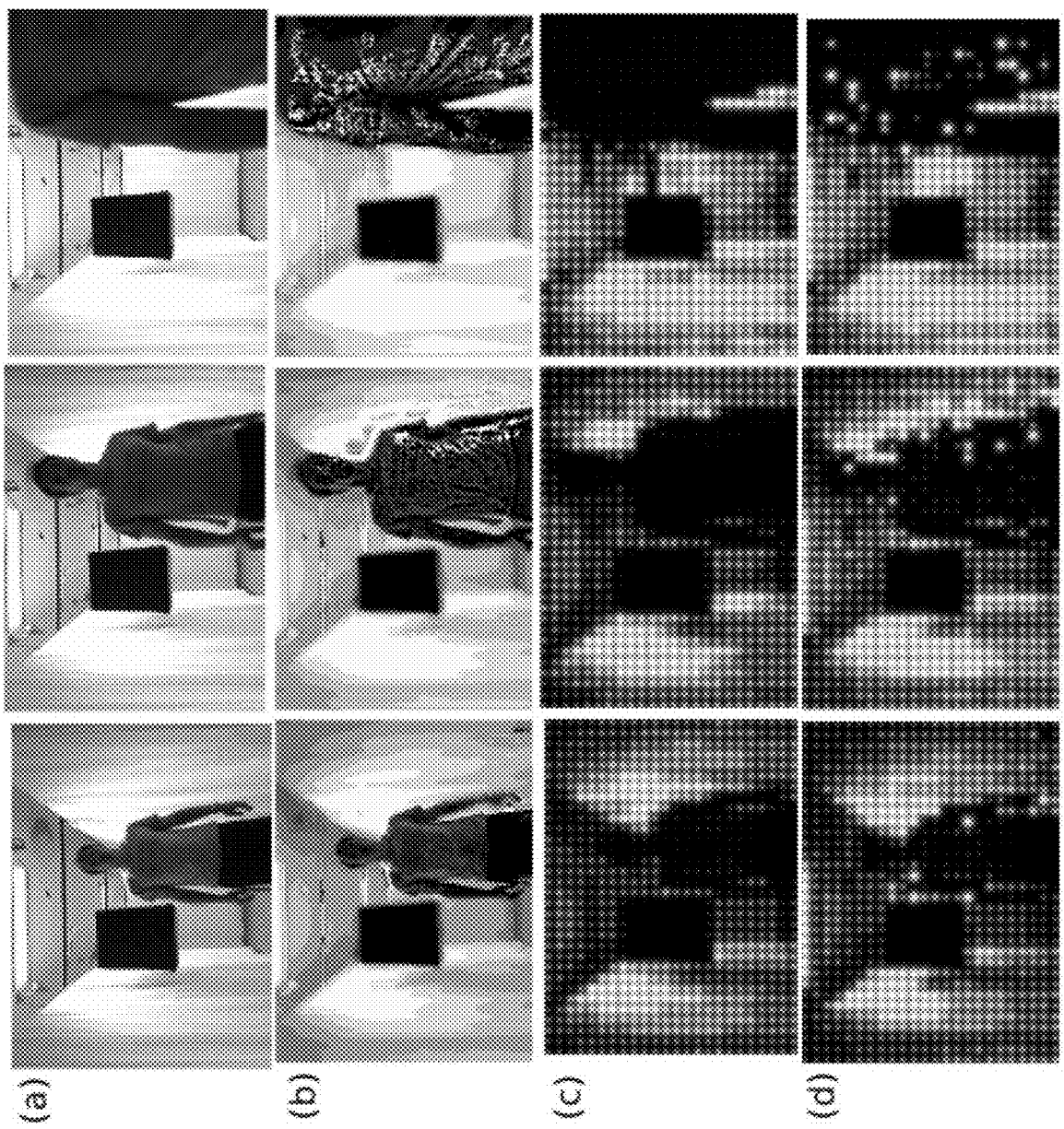
FIG. 12 illustrates an example comparison between the method according to the present disclosure and other methods.

FIG. 12 shows representative example results from the sequence using the method according to present disclosure and histogram equalisation. The contrast enhancement is clearly evident across the body of the walker as he approaches the camera.

Note that the contrast enhancement also increases as the walker gets closer, providing an interpretable cue for looming motion. Significantly less contrast is evident in histogram equalised images.

The Vision Aid System—Example 1

Figure 13:
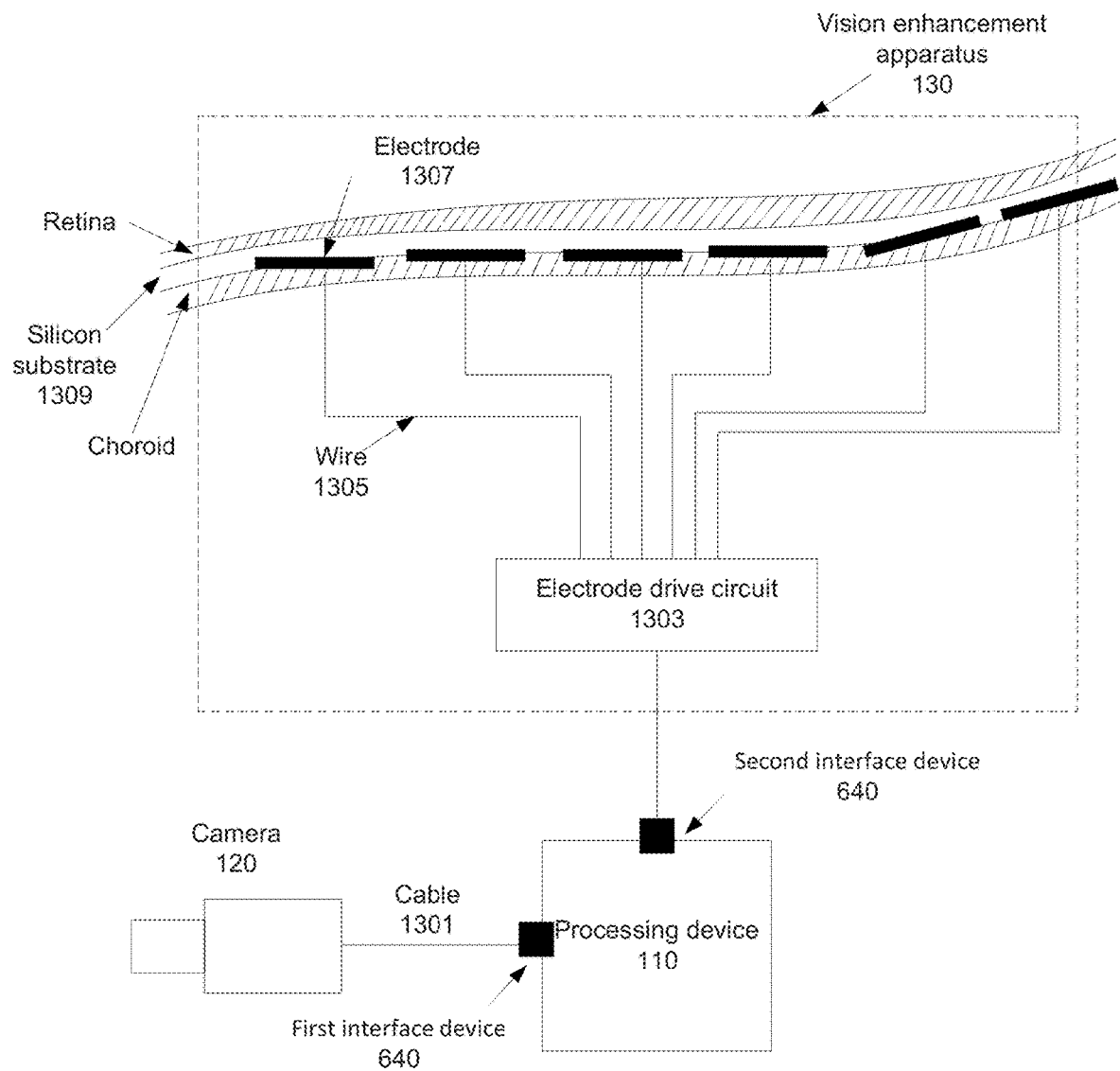
FIG. 13 illustrates an example machine structure of the vision aid system according to the present disclosure.

FIG. 13 illustrates an example machine structure of the vision aid system 100.

In FIG. 13, the camera 120 is a head-mounted camera that is able to be fixed to the head of the vision impaired user 140, which serves the purposes of capturing the input image 150. The input image 150 can be a still image or a frame in a video. As described above, the intensity level of each point in the input image 150 may be represented by a grey level or a RGB value in a RGB space, or any other suitable way without departing from the scope of the present disclosure.

The processing device 110 is a device as described with reference to FIG. 6. A cable 1301 connects the camera 120 to a first interface device 640 of the processing device 110 via which the input image 150 is sent to the processing device 110. On the other hand, a second interface device 640 of the processing device 110 interfaces with the vision enhancement apparatus 130 to apply the intensity levels of the points of the output image 160 to the vision enhancement apparatus 130.

The vision enhancement apparatus 130 includes an electrode drive circuit 1303, multiple wires 1305 and multiple electrodes 1307 and a silicon substrate 1309.

Although there are only six wires 1305 and six electrodes 1307 shown in FIG. 13 for illustration purposes, there can be more wires 1305 and electrodes 1307 in the vision enhancement apparatus 130. The diameters of the electrodes 1307 may be different, for example, 600 μm or 400 μm. The electrodes 1307 may be recessed from the silicon substrate 1309 by for example 50 μm.

Figure 15:
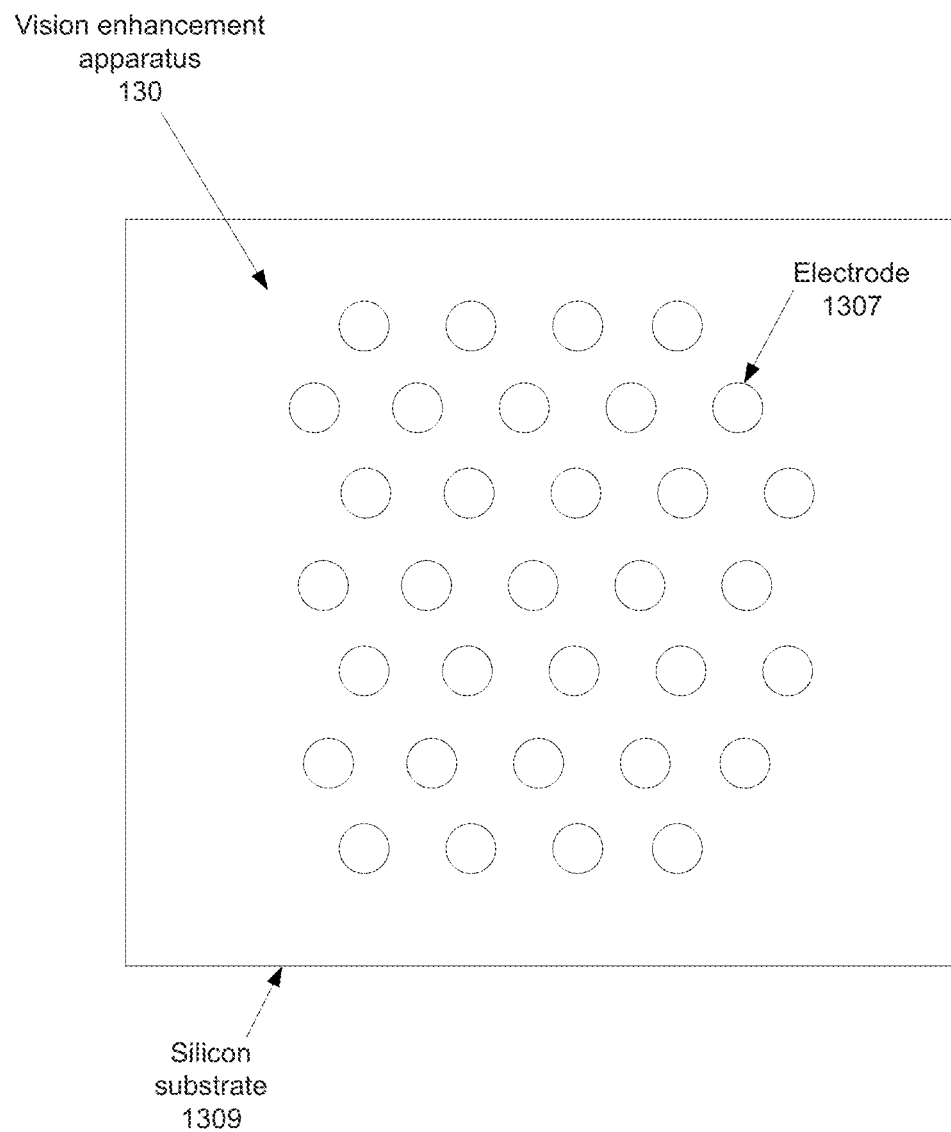
FIG. 15 illustrates an example pattern in which electrodes in the vision aid system are arranged.

FIG. 15 illustrates an example pattern 1500 in which the electrodes 1307 are arranged. In this example, there are 33 electrodes 1307 arranged in a hexagon pattern. The electrodes 1307 may be arranged in other patterns without departing from the scope of the present disclosure.

The electrode drive circuit 1303 receives the intensity levels of the points of the output image 160 from the processing device 110 via the second interface device 640.

The electrode drive circuit 1303 is connected to individual electrodes 1307 via individual wires 1305. The electrodes 1307 are connected to the silicon substrate 1309. The electrodes 1307 are the imaging elements and are made of materials with good electrical conductivity, for example, platinum, while the wires 1305 are individually insulated and may be made of platinum or iridium.

As described above, the vision enhancement apparatus 130 in this example is implanted behind the retina, particularly, between the retina and the choroid of the eyes of the vision impaired user 140, as shown in FIG. 13.

Upon application of the intensity levels of the points of the output image 160 to the vision enhancement apparatus 130, the electrode drive circuit 1303 translates the intensity levels to appropriate electric current or voltage signals to drive the electrodes 1307 to stimulate the retina of the vision impaired user 140.

Therefore, environmental conditions or a media that is being viewed by the vision impaired user 140, which are represented by the input image 150, are better perceived by the vision impaired user 140, as described above.

The Vision Aid System—Example 2

Figure 14:
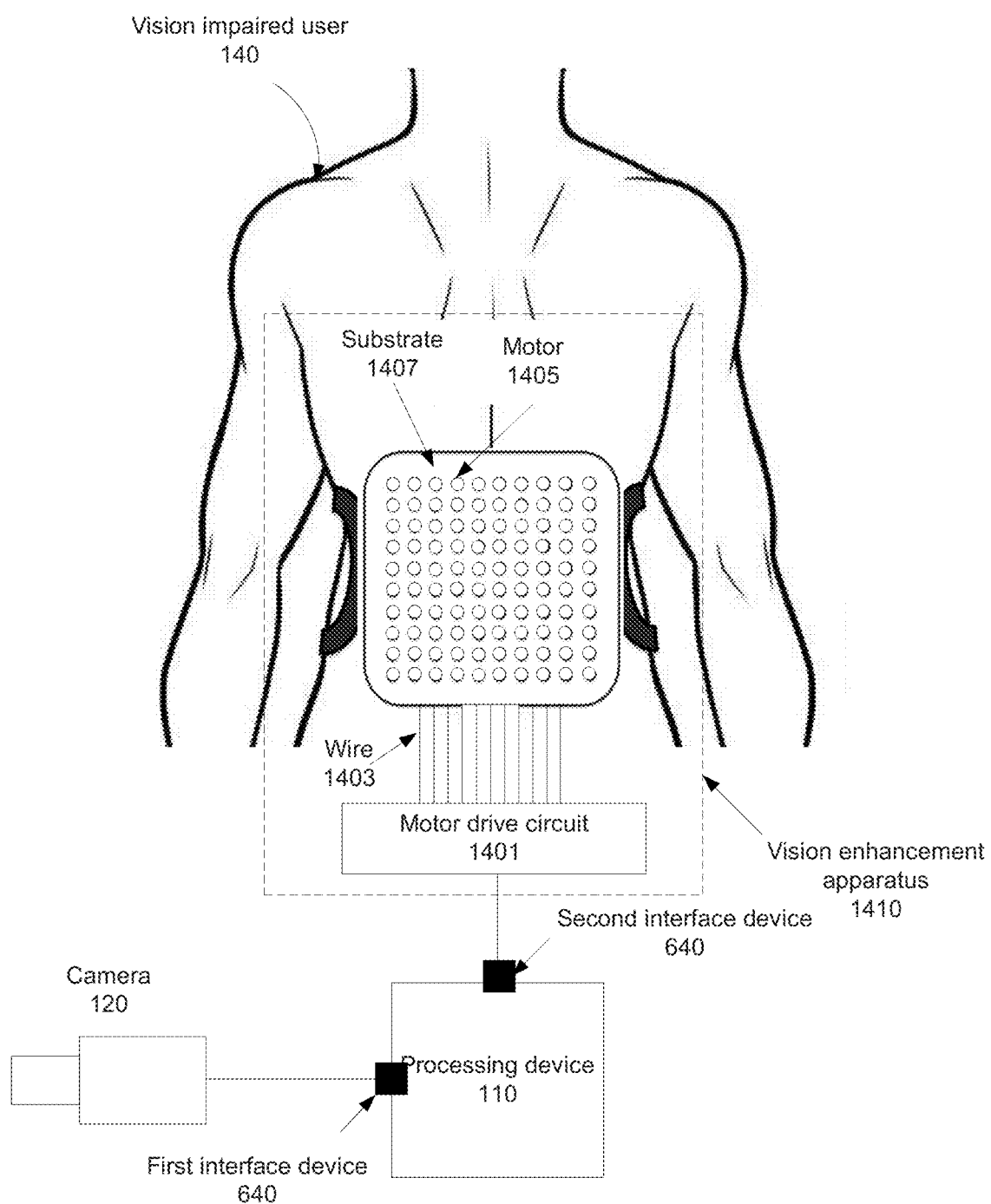
FIG. 14 illustrates a further example machine structure of the vision aid system according to the present disclosure.

The methods described above with reference to FIGS. 2, 3 and 5 are not only applicable to the vision aid system 100 shown in FIG. 13, FIG. 14 illustrates a further example machine structure of vision aid system 1400 to which the methods described above are also applicable.

In the vision aid system 1400 shown in FIG. 14, the camera 120 and the processing device 110 are essentially the same as those in the vision enhancement apparatus 100 shown in FIG. 13. However, the vision enhancement apparatus 1410 of the vision aid system 1400 is different from the vision enhance apparatus 130 shown in FIG. 13. Particularly, the vision enhancement apparatus 1410 that is connected to the processing device 110 via the second interface device 640 is worn by the vision impaired user 140 on his lower back instead of being implanted in the eyes of the vision impaired user 140.

The vision enhancement apparatus 1410 includes a motor drive circuit 1401, wires 1403, an array of motors 1405 and a substrate 1407.

The motors 1405 include vibration motors, for example, coin motors manufactured by Precision Microdrives Ltd., London, UK. The motors 1405 may be driven by direct current for easy implementation purposes. Vibration output of the motors 1405 is controlled by adjusting the voltage (0-5 Voltages) across the motor 1405 by using pulse width modulation on an 8-bit (256-step) scale. A stimulus level may be expressed in percent duty cycle (0-100%), which is equivalent to the percentage of time the 20 kHz power signal is active (5 Voltages), averaged over a given period of time. An initial one millisecond (ms) overdrive at maximal duty cycle (100%) may be used during each stimulus to enhance motor acceleration and increase stimulation reliability at lower duty cycles.

As shown in FIG. 14, the motors 1405 are arranged in a 10×10 square pattern. The motors 1405 may be arranged in other patterns without departing from the scope of the present disclosure.

Ideally, each pixel of the input image 150 correspond to one motor 1405, however it is usually impractical to have a large number of motors 1405 placed on the lower back of the vision-impaired user 140. For example, if the input image 150 is an image of 100×100 pixels, the vision enhancement apparatus 1410 needs to include 10,000 motors 1405 to have one to one relationship to the input image 150, which is usually too expensive and may cause physical burden to the user 140. In this case, the input image 150 is down-sampled by the camera 120 or the processing device 110 to match the resolution of the vision enhancement apparatus 1410, i.e., 10×10 in this example.

The input image 150 with the right resolution is processed by the processing device 110 according to the method described above with reference to FIGS. 2, 3, and 5 to produce the output image 160.

The motor drive circuit 1401 receives the intensity levels of the points of the output image 160 from the processing device 110 via the second interface device 640. The motor drive circuit 1401 translates the intensity levels to appropriate electric current or voltage signals to drive the motors 1405 to generate vibrations on the lower back of the vision-impaired user 140. The vibrations generated by the motors 1405 form a tactile pattern corresponding to the input image 150 on the lower back of the vision-impaired user 140.

Therefore, environmental conditions or a media that is being viewed by the vision impaired user 140, which are represented by the input image 150, can be better perceived by the vision impaired user 140 in the form of tactility.

It should also be understood that, unless specifically stated otherwise as apparent from the following discussion, it is appreciated that throughout the description, discussions utilizing terms such as "obtaining" or "determining" or "sending" or "receiving" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The invention claimed is:

1. A computer-implemented method for enhancing vision for a vision impaired user, the method comprising: receiving an input image having a plurality of points;
   generating an importance map having a plurality of points for the input image, wherein each point in the importance map corresponds to a point in the input image and represents a visual importance of that point in the input image;
   for each point in the input image, determining a weight for the input image point based on the corresponding point in the importance map;
   comparing the weight for each point to a threshold;
   when the weight for a point meets the threshold, determining a first output value for an imaging element of a vision enhancement apparatus so that a difference between the first output value and an intensity level of a portion of the input image neighbouring the point increases with the weight, wherein the difference is at least one just-noticeable-difference of the vision enhancement apparatus, such that when the first output value is applied to the imaging element of the vision enhancement apparatus to create a first visual stimulus, the first visual stimulus is substantially perceivable by the vision impaired user; and
   applying the first output value to the imaging element.

2. The computer-implemented method according to claim 1, wherein the intensity level of the portion of the input image neighbouring the point is determined by calculating an average intensity level of points in the portion of the input image.

3. The computer-implemented method according to claim 1, wherein:
   when an intensity level of the point is greater than the intensity level of the portion of the input image, the first output value is greater than the intensity level of the portion of the input image.

4. The computer-implemented method according to claim 3, wherein:

if the intensity level of the point is less than the intensity level of the portion of the input image, the first output value is less than the intensity level of the portion of the input image.

5. The computer-implemented method according to claim 3, wherein:
when the intensity level of the point is equal to the intensity level of the portion of the input image, the first output value is such that the difference is at least one just-noticeable-difference of the vision enhancement apparatus.

6. The computer-implemented method according to claim 3, further comprising:
determining a difference between the intensity level of the point and the intensity level of the portion of the input image,
when the difference is greater than at least one just-noticeable-difference of the vision enhancement apparatus, the first output value for the imaging element is equal to the intensity level of the point.

7. The computer-implemented method according to claim 1, further comprising:
determining the just-noticeable-difference of the vision enhancement apparatus based on a Weber fraction and the intensity level of the portion of the input image.

8. The computer-implemented method according to claim 1, wherein the difference between the first output value and the intensity level of the portion of the input image neighbouring the point exponentially increases with the weight.

9. The computer-implemented method according to claim 1, further comprising:
when the weight does not meet the threshold, determining a second output value for the imaging element based on the weight and the threshold and applying the second output value to the imaging element, wherein a difference between the second output value and the intensity level of the portion of the input image is less than a difference between the intensity level of the point and the intensity level of the portion of the input image, such that when the second output value is applied to the imaging element to create a second visual stimulus, the second visual stimulus is less perceivable by the vision impaired user.

10. The computer-implemented method according to claim 9, wherein:
when the intensity level of the point is greater than the intensity level of the portion of the input image, the second output value is greater than the intensity level of the portion of the input image.

11. The computer-implemented method according to claim 9, wherein:
when the intensity level of the point is less than the intensity level of the portion of the input image, the second output value is less than the intensity level of the portion of the input image.

12. The computer-implemented method according to claim 9, wherein:
when the intensity level of the point is equal to the intensity level of the portion of the input image, the second output value is determined to the intensity level of the point.

13. The computer-implemented method according to claim 1, further comprising:
when the weight does not meet the threshold, determining a third output value for the imaging element that is equal to the intensity level of the point applying the third output value to the imaging element.

14. The computer-implemented method according to claim 1, further comprising:
down-sampling the input image to match a resolution of the vision enhancement apparatus.

15. The computer-implemented method according to claim 1, wherein the imaging element of the vision enhancement apparatus comprises an electrode.

16. The computer-implemented method according to claim 15, the method further comprising:
implanting the electrode at a suitable location in a body of the vision impaired user; and
applying the first output value to the electrode to create the first visual stimulus.

17. The computer-implemented method according to claim 16, wherein implanting the electrode comprises implanting the electrode at one of the following locations in the body of the vision impaired user:
a subretinal location,
an epiretinal location,
an intra-scleral location,
a suprachoroidal space, and
a cerebral cortex location.

18. The computer-implemented method according to claim 15, the method further comprises placing the electrode on a tongue of the vision impaired user to create the first visual stimulus.

19. The computer-implemented method according to claim 1, wherein the imaging element of the vision enhancement apparatus is a motor, the method further comprising;
placing the motor at suitable location on a body of the vision impaired user; and
applying the first output value to the motor to create the first visual stimulus.

20. The computer-implemented method according to claim 19, wherein placing the motor comprises placing the motor at one of the following locations on the body of the vision impaired user:
a back, and
chest.

21. A non-transitory computer readable medium comprising computer-executable instructions stored thereon, that when executed by a processor, causes the processor to perform the method of claim 1.

22. A computer system for applying a signal to a vision enhancement apparatus, the computer system comprising:
the vision enhancement apparatus having an imaging element;
a memory configured to store instructions;
an interface device;
a processor configured to receive an input image having a plurality of points;
generate an importance map having a plurality of points for the input image, wherein each point in the importance map corresponds to a point in the input image and represents a visual importance of that point in the input image;
for each point in the input image, determining a weight for the input image point based on the corresponding point in the importance map;
compare the weight for each point to a threshold;
when the weight for the point meets the threshold, determine a first output value for the imaging element of the vision enhancement apparatus so that a difference between the first output value and an intensity level of a portion of the input image neighbouring the point increases with the weight, wherein the difference is at least one just-noticeable-difference of the vision enhancement apparatus, such that when the first output value is applied to the imaging element of the vision enhancement apparatus to create a first visual stimulus, the first visual stimulus is substantially perceivable by the vision impaired user; and apply the first output value to the imaging element using the interface device.

23. The computer system according to claim 22, wherein the imaging element of the vision enhancement apparatus is an electrode that is suitable for implantation in a body of the vision impaired user to create the first visual stimulus.

24. The computer system according to claim 23, wherein the electrode is suitable for implantation in a subretinal location, an epiretinal location, an intra-scleral location, a suprachoroidal space, and a cerebral cortex location.

25. The computer system according to claim 22, wherein the imaging element of the vision enhancement apparatus is an electrode that is suitable for placement on a tongue of the vision impaired user to create the first visual stimulus.

26. The computer system according to claim 22, wherein the imaging element of the vision enhancement apparatus is a motor that is suitable for placement on a body of the vision impaired user to create the first visual stimulus.

27. The computer system according to claim 26, wherein the motor is suitable for placement on a back or chest of the vision impaired user.

* * * * *